United States Patent
Boruah et al.

(10) Patent No.: US 9,000,007 B2
(45) Date of Patent: Apr. 7, 2015

(54) 5-BENZYLAMINOMETHYL-6-AMINOPYRAZOLO [3, 4 -B] PYRIDINE DERIVATIVES AS CHOLESTERYL ESTER-TRANSFER PROTEIN (CETP) INHIBITORS USEFUL FOR THE TREATMENT OF ATHEROSCLEROSIS

(71) Applicant: Dr. Reddy's Laboratories, Ltd., Hyderabad (IN)

(72) Inventors: Anima Boruah, Hyderabad (IN); Shanavas Alikunju, Secunderabad (IN)

(73) Assignee: Dr. Reddy's Laboratories Ltd., Hyderabad (IN)

( * ) Notice: Subject to any disclaimer, the term of this patent is extended or adjusted under 35 U.S.C. 154(b) by 0 days.

(21) Appl. No.: 14/347,519

(22) PCT Filed: Sep. 27, 2012

(86) PCT No.: PCT/IB2012/002435
§ 371 (c)(1),
(2) Date: Mar. 26, 2014

(87) PCT Pub. No.: WO2013/046045
PCT Pub. Date: Apr. 4, 2013

(65) Prior Publication Data
US 2014/0288072 A1    Sep. 25, 2014

Related U.S. Application Data

(60) Provisional application No. 61/558,262, filed on Nov. 10, 2011.

(30) Foreign Application Priority Data

Sep. 27, 2011    (IN) ............................ 3337/CHE/2011

(51) Int. Cl.
C07D 401/14    (2006.01)
A61K 31/437    (2006.01)
C07D 471/04    (2006.01)

(52) U.S. Cl.
CPC .................................. C07D 471/04 (2013.01)

(58) Field of Classification Search
CPC ........................... C07D 401/14; A61K 31/437
USPC .......................................... 546/119; 514/303
See application file for complete search history.

(56) References Cited

U.S. PATENT DOCUMENTS

| | | |
|---|---|---|
| 2,858,309 A | 10/1958 | Druey et al. |
| 2,965,643 A | 12/1960 | Druey et al. |
| 3,546,295 A | 12/1970 | Maravetz |
| 5,086,073 A | 2/1992 | White et al. |
| 5,260,331 A | 11/1993 | White et al. |
| 5,332,759 A | 7/1994 | Depreux et al. |
| 5,348,953 A | 9/1994 | Doherty et al. |
| 5,422,355 A | 6/1995 | White et al. |
| 5,456,923 A | 10/1995 | Nakamichi et al. |
| 5,474,989 A | 12/1995 | Hashimoto et al. |
| 5,482,967 A | 1/1996 | Natsugari et al. |
| 5,491,152 A | 2/1996 | Wilde et al. |
| 5,545,608 A | 8/1996 | Morimoto et al. |
| 5,807,885 A | 9/1998 | Gentile et al. |
| 5,856,347 A | 1/1999 | Hashiguchi et al. |
| 5,892,114 A | 4/1999 | Goldmann et al. |
| 5,977,170 A | 11/1999 | Commons et al. |
| 5,985,326 A | 11/1999 | Butler |
| 6,008,231 A | 12/1999 | Lebaut et al. |
| 6,008,362 A | 12/1999 | Commons et al. |
| 6,121,271 A | 9/2000 | Dollings et al. |
| 6,218,431 B1 | 4/2001 | Schoen et al. |
| 6,306,911 B1 | 10/2001 | Wachter et al. |
| 6,350,786 B1 | 2/2002 | Albano et al. |
| 6,407,111 B1 | 6/2002 | Bos et al. |
| 6,432,987 B2 | 8/2002 | Gunther et al. |

(Continued)

FOREIGN PATENT DOCUMENTS

| | | |
|---|---|---|
| AU | 660026 | 6/1995 |
| EP | 0298666 A2 | 1/1989 |

(Continued)

OTHER PUBLICATIONS

International Search Report and Written Opinion dated Feb. 25, 2013, for corresponding International Patent Application No. PCT/IB2012/002435.

(Continued)

*Primary Examiner* — Niloofar Rahmani
(74) *Attorney, Agent, or Firm* — Pergament Gilman & Cepeda LLP; Milagros A. Cepeda; Edward D. Pergament

(57) ABSTRACT

The present application relates to a series of substituted pyrazolopyridin-6-amines having the general formula (I), including their stereoisomers and/or their pharmaceutically acceptable salts. Wherein R, $R^1$, $R^2$, $R^a$, $R^{aa}$, $R^b$ and n are as defined herein. The present invention further relates to pharmaceutical compositions comprising compounds of formula (I). The compounds of this application are useful as CETP inhibitors for increasing HDL cholesterol and decreasing LDL cholesterol in a patient.

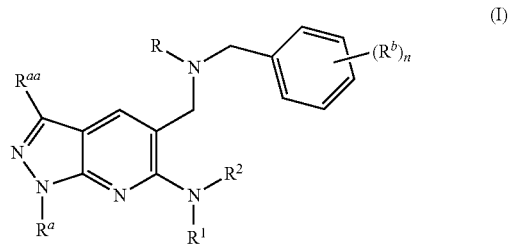

(I)

12 Claims, No Drawings

(56) References Cited

U.S. PATENT DOCUMENTS

| | | |
|---|---|---|
| 6,448,290 B1 | 9/2002 | Ohuchida et al. |
| 6,488,922 B1 | 12/2002 | Damm et al. |
| 6,489,478 B1 | 12/2002 | DeNinno et al. |
| 6,498,172 B1 | 12/2002 | Cameron et al. |
| 6,548,555 B1 | 4/2003 | Curatolo et al. |
| 6,576,644 B2 | 6/2003 | Bi et al. |
| 6,638,522 B1 | 10/2003 | Mulye |
| 6,642,252 B2 | 11/2003 | Bisacchi et al. |
| 6,710,089 B2 | 3/2004 | Sikorski et al. |
| 6,713,499 B2 | 3/2004 | Flohr et al. |
| 6,723,753 B2 | 4/2004 | Sikorski et al. |
| 6,730,679 B1 | 5/2004 | Roy et al. |
| 6,962,931 B2 | 11/2005 | Gumkowski et al. |
| 7,008,640 B2 | 3/2006 | Watanabe et al. |
| 7,012,081 B2 | 3/2006 | Krueger et al. |
| 7,034,013 B2 | 4/2006 | Thompson et al. |
| 7,037,528 B2 | 5/2006 | Kipp et al. |
| 7,078,057 B2 | 7/2006 | Kerkhof |
| 7,081,255 B2 | 7/2006 | Baert et al. |
| 7,276,610 B2 | 10/2007 | Huang et al. |
| 7,332,514 B2 | 2/2008 | Maeda et al. |
| 7,459,470 B2 | 12/2008 | Ernst et al. |
| 7,470,705 B2 | 12/2008 | Bell et al. |
| 7,579,365 B2 | 8/2009 | Nickel et al. |
| 7,619,096 B2 | 11/2009 | Beadle et al. |
| 7,737,295 B2 | 6/2010 | Ali et al. |
| 7,781,443 B2 | 8/2010 | Kubota et al. |
| 8,030,359 B2 | 10/2011 | Geers et al. |
| 8,158,640 B2 | 4/2012 | Kubota et al. |
| 8,389,011 B2 | 3/2013 | Crew et al. |
| 2002/0052363 A1 | 5/2002 | Dinsmore et al. |
| 2002/0177587 A1 | 11/2002 | Bi et al. |
| 2002/0193283 A1 | 12/2002 | Dinsmore et al. |
| 2003/0054037 A1 | 3/2003 | Babcock et al. |
| 2003/0072801 A1 | 4/2003 | Curatolo et al. |
| 2003/0104063 A1 | 6/2003 | Babcock et al. |
| 2003/0114454 A1 | 6/2003 | Sikorski et al. |
| 2003/0170309 A1 | 9/2003 | Babcock et al. |
| 2003/0198674 A1 | 10/2003 | Curatolo et al. |
| 2004/0039018 A1 | 2/2004 | Ruggeri |
| 2004/0053842 A1 | 3/2004 | Nguyen et al. |
| 2004/0176446 A1 | 9/2004 | Alonso-Alija et al. |
| 2004/0185102 A1 | 9/2004 | Friesen et al. |
| 2005/0038007 A1 | 2/2005 | Curatolo et al. |
| 2005/0049239 A1 | 3/2005 | Huang et al. |
| 2005/0059810 A1 | 3/2005 | Maeda et al. |
| 2005/0153964 A1 | 7/2005 | Leach et al. |
| 2006/0178514 A1* | 8/2006 | Baruah et al. .......... 544/406 |
| 2007/0015758 A1* | 1/2007 | Baruah et al. .......... 514/241 |
| 2009/0118328 A1 | 5/2009 | Friesen et al. |
| 2009/0227580 A1 | 9/2009 | Kishida et al. |
| 2009/0239865 A1 | 9/2009 | Chang et al. |
| 2010/0249148 A1 | 9/2010 | Ohgiya et al. |
| 2011/0189210 A1 | 8/2011 | Okamoto et al. |

FOREIGN PATENT DOCUMENTS

| | | |
|---|---|---|
| EP | 0585500 A1 | 3/1994 |
| EP | 0604798 A1 | 7/1994 |
| EP | 1108426 A2 | 6/2001 |
| EP | 1741424 A2 | 1/2007 |
| GB | 2087390 A | 5/1982 |
| JP | 01104052 H | 4/1989 |
| JP | 07285962 H | 10/1995 |
| JP | 0892224 H | 4/1996 |
| JP | 0892225 H | 4/1996 |
| JP | 11209366 H | 8/1999 |
| WO | 93/00332 | 1/1993 |
| WO | 94/05648 | 3/1994 |
| WO | 96/02509 A1 | 2/1996 |
| WO | 98/57925 | 12/1998 |
| WO | 98/57927 | 12/1998 |
| WO | 98/57928 | 12/1998 |
| WO | 01/00623 A1 | 1/2001 |
| WO | 01/02350 A2 | 1/2001 |
| WO | 01/22954 A2 | 4/2001 |
| WO | 02/22584 A1 | 3/2002 |
| WO | 02/068417 A2 | 9/2002 |
| WO | 03/030909 A1 | 4/2003 |
| WO | 03/063832 A1 | 8/2003 |
| WO | 2004/073709 A1 | 9/2004 |
| WO | 2004/078128 A2 | 9/2004 |
| WO | 2004/078169 A1 | 9/2004 |
| WO | 2006073973 * | 7/2006 |
| WO | 2007/075194 A1 | 7/2007 |
| ZA | 9204659 | 3/1993 |

OTHER PUBLICATIONS

Gordon et al., "High-Density Lipoprotein Cholesterol and Cardiovascular Disease—Four Prospective American Studies", Circulation, Jan. 1989, pp. 8-15, vol. 79—issue No. 1, American Heart Association.

Despres et al., "HDL-cholesterol as a marker of coronary heart disease risk: the Quebec cardiovascular study", Atherosclerosis, 2000, pp. 263-272, vol. 153, Elsevier Science Ireland Ltd.

International Search Report and Written Opinion dated May 8, 2013, for corresponding International Patent Application No. PCT/IB2012/002056.

International Search Report and Written Opinion dated Mar. 27, 2014, for corresponding International Patent Application No. PCT/IB2013/002909.

Tae-Wan Kim et al., "Modified Release of Coated Sugar Spheres Using Drug-Containing Polymeric Dispersions", Arch Pharm Res, 2007, pp. 124-130, vol. 30—issue No. 1.

Tae-Wan Kim et al., "Characterization of Dual Layered Pellets for Sustained Release of Poorly Water-Soluble Drug", Chem. Pharm. Bull., Jul. 2007, pp. 975-979, vol. 55—issue No. 7, Pharmaceutical Society of Japan.

Toshiya Kai et al., "Oral Absorption Improvement of Poorly Soluble Drug Using Solid Dispersion Technique", Chem. Pharm. Bull., Mar. 1996, pp. 568-571, vol. 43—issue No. 3, Pharmaceutical Society of Japan.

Tomaz Einfalt et al., "Methods of amorphization and investigation of the amorphous state", Acta Pharm., 2013, pp. 305-334, vol. 63.

Al-Dabbagh and Smith, "Species Differences in Oxidative Drug Metabolism: Some Basic Considerations", Archives of Toxicology, 1984, pp. 219-231, Suppl. 7, Springer-Verlag.

Hans Bundgaard, "Design of prodrugs: Bioreversible derivatives for various functional groups and chemical entities", Design of Prodrugs, 1985, p. 1, Elsevier Science Publishers B.V. (Biomedical Division).

Richard B. Silverman, "Prodrugs and Drug Delivery Systems", The Organic Chemistry of Drug Design and Drug Action, 1992, pp. 352-400, Academic Press, Inc.

Vippagunta et al., "Crystalline Solids", Advanced Drug Delivery Reviews, 2001, pp. 3-26, vol. 48, Elsevier Science B.V.

Extended European Search Report dated Jun. 22, 2010, for corresponding European Patent Application No. 06 77 4300.

Kerns and Di, "Permeability Structure Modification Strategies", Drug-like Properties: Concepts, Structure Design and Methods: from ADME to Toxicity Optimization, 2008, pp. 92-93, Elsevier Inc.

Goosen et al., "Physiochemical Characterization and Solubility Analysis of Thalidomide and Its N-Alkyl Analogs", Pharmaceutical Research, Jan. 1, 2002, pp. 13-19, vol. 19—issue No. 1, Plenum Publishing Corporation.

Fourie et al., "Percutaneous delivery of carbamazepine and selected N-Alkyl and N-hydroxyalkyl analogues", International Journal of Pharmaceutics, 2004, pp. 59-66, vol. 279, Elsevier B.V.

Edwards et al., "Nonpeptidic Inhibitors of Human Neutrophil Elastase. 7. Design, Synthesis, and in Vitro Activity of a Series of Pyridopyrimidine Trifluromethyl Ketones", Journal of Medicinal Chemistry, 1996, pp. 1112-1124, vol. 39—issue No. 5, American chemical Society.

Rautio et al., "Piperazinylalkyl prodrugs of naproxen improve in vitro skin permeation", European Journal of Pharmaceutical Sciences, 2000, pp. 157-163, vol. 11, Elsevier Science B.V.

(56) References Cited

OTHER PUBLICATIONS

Anzini et al., "Mapping and Fitting the peripheral Benzodiazepine Receptor Binding Site by Carboxamide Derivatives. Comparison of Different Approaches to Quantitative Ligand-Receptor Interaction Modeling", J. Med. Chem., 2001, pp. 1134-1150, vol. 44—issue No. 8, American Chemical Society.

Sculley and Hamilton, "Some Amide Derivatives of Certain Aminomethylpyridines", J. American Chem. Soc., Jul. 20, 1953, pp. 3400-3403, vol. 75.

Berge et al., "Pharmaceutical Salts", Review Article, Journal of Pharmaceutical Studies, Jan. 1977, p. 1-19, vol. 66—issue No. 1.

Derry E. V. Wilman, "Prodrugs in cancer chemotheraphy", Action Cancer Guest Lecture, Biochemical Society Transactions, 615th Meeting, Belfast, 1986, pp. 375-385, vol. 14.

Stella and Himmelstein, "Prodrugs: A Chemical Approach to Targeted Drug Delivery", Directed Drug Delivery—A Multidisciplinary Problem, 1985, pp. 247-267, Humana Press, Clifton, New Jersey.

Ali et al., "An Efficient and Facile Synthesis of 2-Chloro-3-formyl Quinolines from Acetanilides in Micellar Media by Vilsmeier-Haack Cyclisation", Letter, Synlett, 2001, pp. 251-253, issue No. 2, Thieme Stuttgart, New York.

John B. Paine III, "A Convenient Synthesis of Nicotinate Esters from 3-Cyanopyridones", J. Heterocyclic Chem., 1987, pp. 351-355, vol. 24.

Boatman et al., "Alkylations at the Methyl or α-Methylene Group of 6- or 4-Alkyl-3-cyano-2(1)-pyridones through Dianions", J. Organic Chemistry, Nov. 1965, pp. 3593-3597, vol. 30.

Cappelli et al., "Design, Synthesis, Structural Studies, Biological Evaluation, and Computational Simulations of Novel Potent AT1 Angiotensin II Receptor Antagonists Based on the 4-Phenylquinolines Structure", J. Med. Chem., 2004, pp. 2574-2586, vol. 47—issue No. 10, American Chemical Society.

Izumi et al., "1H-Imidazo[4,5-c]quinoline Derivatives as Novel potent TNF-α Suppressors: Synthesis and Structure-Activity Relationship of 1-, 2- and 4-Substituted 1H-imidazo[4,5-c]quinolines or 1H-imidazo[4,5-c]pyridines", Bioorganic & Medicinal Chemistry, 2003, pp. 2541-2550, vol. 11, Elsevier Science Ltd.

Yin and Buchwald, "Palladium-Catalyzed Intermolecular Coupling of Aryl Halides and Amides", Organic Letters, 2000, pp. 1101-1104, vol. 2—issue No. 8, American Chemical Society.

Robert Franzen, "The Suzuki, the Heck, and the Stille reaction—three versatile methods for the introduction of new C—C bonds on solid support", Can. J. Chem., 2000, pp. 957-962, vol. 78, NRC Canada.

Negishi et al., "Cyclic Carbopalladation. A Versatile Synthetic Methodology for the Construction of Cyclic Organic Compounds", Chemical Reviews, 1996, pp. 365-393, vol. 96—issue No. 1, American Chemical Society.

McGee, Jr. et al., "Fusicoccin Synthesis by Intramolecular [4+4] Photocycloaddition of 2-Pyridones: Stereocontrol of the Cycloaddition and Elaboration of the Pentacyclic Product", Paper, Synthesis, Jun. 18, 2001, pp. 1185-1196, issue No. 8, Georg Thieme Verlag Stuttgart, New York.

Bisgaier et al., "Use of flourescent cholesteryl ester microemulsions in cholesteryl ester transfer protein assays", Paper on Methodology, Journal of Lipid Research, 1993, pp. 1625-1634, vol. 34.

Epps et al., "Method for measuring the activities of cholesteryl ester transfer protein (lipid transfer protein)", Chemistry and Physics of LIPIDS, 1995, pp. 51-63, vol. 77, Elsevier Science Ireland Ltd.

Derwent World Patent Index Search Results, obtained from Delphion website (www.delphion.com), 5 pages.

INPADOC/Family and Legal Status Search Results, obtained from Dialog Database #345, Jun. 14, 2006, 19 pages.

International Search Report and Written Opinion dated Oct. 23, 2006, for corresponding International Patent Application No. PCT/US06/25427.

* cited by examiner

5-BENZYLAMINOMETHYL-6-AMINOPYRAZOLO [3, 4 -B] PYRIDINE DERIVATIVES AS CHOLESTERYL ESTER-TRANSFER PROTEIN (CETP) INHIBITORS USEFUL FOR THE TREATMENT OF ATHEROSCLEROSIS

This application is a National Stage Application under 35 U.S.C. §371 of PCT International Application No. PCT/IB2012/002435 filed Sep. 27, 2012, which claims the benefits of Indian Provisional Application No. 3337/CHE/2011, filed Sep. 27, 2011 and U.S. Provisional Application No. 61/558,262 filed Nov. 10, 2011, all of which are hereby incorporated by reference in their entireties.

TECHNICAL FIELD

The present application relates to substituted pyrazolopyridin-6-amines of formula (I) or stereoisomers thereof or pharmaceutically acceptable salts thereof.

BACKGROUND

Cholesteryl ester-transfer protein (CETP) is an important player in metabolism of lipoproteins such as, for example, a high density lipoprotein (HDL). CETP is a 70 kDa plasma glycoprotein that is physically associated with HDL particles. It facilitates the transport of cholesteryl ester from HDL to apolipoprotein B-containing lipoproteins. This transfer is accompanied by transfer of triglycerides in the opposite direction. Thus, a decrease in CETP activity can result in an increase in the level of HDL cholesterol and a decrease in the level of very low density lipoprotein (VLDL) and low density lipoprotein (LDL). CETP can therefore simultaneously affect the concentrations of pro-atherogenic (e.g., LDL) and anti-atherogenic (e.g., HDL) lipoproteins.

Clinical studies in humans have shown that inhibitors of CETP can be effective in elevating HDL levels by 30-110%. Further, epidemiological studies have shown that low high-density lipoprotein cholesterol (HDL-C) levels is a powerful risk factor for coronary artery disease (CAD). See generally, Gordon et al., Circulation, 79, pp. 8-15, 1989; Despres et al., Atherosclerosis 153: 263-272, 2000. Elevating HDL-C has been shown to decrease this risk and it is estimated that each 1 mg/dl (0.02 mmol/l) elevation of HDL-C is associated with a 2-3% reduction in coronary heart disease (CHD) risk, a magnitude comparable to that for low density lipoprotein (LDL) lowering.

It is believed that the anti-atherogenic role of HDL is in part due to its ability to promote the efflux of free cholesterol from cells and to transport it to the liver, a process termed reverse cholesterol transport. HDL could protect against atherosclerosis by several other mechanisms. For example, several studies have shown that HDL to have antioxidant and anti-inflammatory effects. Oxidative products of lipid metabolism induce inflammatory cell recruitment in vascular cells. HDL particles carry enzymes that retard LDL oxidation, including paraoxonase, platelet-activating factor acetylhydrolase, and lecithin-cholesterol acyltransferase. These enzymes degrade pro-inflammatory, oxidized phospholipids, limiting their accumulation in LDL. In addition, apoA-I can bind oxidized lipids and remove them from LDL. Further, HDL also can act as a carrier vehicle for small molecules, including bacterial lipopolysaccharide (LPS) thus regulating the inflammatory effects of LPS. In animal models of endotoxic shock, HDL attenuates organ injury and adhesion molecule expression. Thus elevating HDL is not only anti-atherogenic but it could also potentially be anti-inflammatory.

Elevation of HDL by CETP inhibition has been described in the art.

However, no CETP inhibitors are currently being marketed. Further, other existing therapies such as, for example, HDL-elevating therapies and anti-atherosclerosis therapies have limitations including serious tolerance issues. Thus, there is a present need to find alternative therapies including methods of preventing or treating conditions or diseases associated with lipoprotein metabolism such as, for example, atherosclerosis.

SUMMARY

Accordingly, the present application relates to substituted pyrazolopyridin-6-amines having the general formula (I):

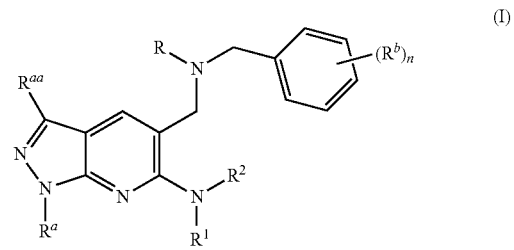

wherein,
R represents hydrogen or

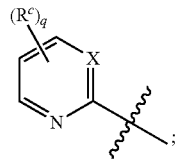

X represents —CH or —N;
$R^1$ and $R^2$ are independently of each other selected from hydrogen, acyl, alkyl or —$(CH_2)_p$-cycloalkyl;
$R^a$ and $R^{aa}$ are independently of each other selected from hydrogen or alkyl;
$R^b$, in each occurrence, is independently selected from halogen, alkyl, haloalkyl, hydroxy, alkoxy or haloalkoxy;
$R^c$, in each occurrence, is independently selected from hydrogen, cyano, halogen, alkyl, alkoxy, haloalkoxy, —$COOR^d$, —$C(=O)$—$R^e$, —$CONR^gR^h$, —$C(=O)$—$CH=CH$—$NR^iR^j$, —$NHCOR^t$, an optionally substituted group selected from cycloalkyl, aryl, heteroaryl or heterocycle ring, wherein the optional substituent, in each occurrence, is selected independently from hydrogen, halogen, cyano, hydroxyl, alkyl, haloalkyl, alkoxy, alkoxyalkyl or haloalkoxy;
$R^d$, $R^e$, $R^g$, $R^h$, $R^i$ and $R^j$, in each occurrence, independently of each other represents hydrogen or alkyl;
$R^t$ is selected from hydrogen, alkyl or cycloalkyl;
n is 0, 1, 2 or 3;
p is 0, 1, or 2; and
q is 1 or 2.

The present application also relates to the process for the preparation of compounds of formula (I).

The present application further describes the compounds of formula (I) as cholesteryl ester-transfer protein (CETP) inhibitors.

The present application further relates to pharmaceutical compositions comprising compounds of formula (I) or stereoisomers thereof or pharmaceutically acceptable salts thereof.

DETAILED DESCRIPTION

As used herein, the expression 'Alkyl' group refers to a linear or branched alkyl group with 1 to 10 carbon atoms. Exemplary alkyl groups include, but are not limited to, methyl, ethyl, n-propyl, iso-propyl, n-butyl, iso-butyl, t-butyl, n-pentyl, iso-pentyl, hexyl, heptyl, octyl and the like.

As used herein, the expression 'Alkoxy' group refers to an —O-(alkyl) group, wherein alkyl group is as defined above. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms.

As used herein, the expression 'Alkoxyalkyl' refers to an alkoxy substituted alkyl group, wherein alkoxy and alkyl groups are as defined above. Typically, the alkoxy group can have from 1 to 10 carbon atoms, and the alkyl group can have from 1 to 10 carbon atoms. Exemplary alkoxyalkyl groups include, but are not limited to, ethoxymethyl, propoxyethyl, ethoxybutyl and the like.

As used herein, the expression 'Acyl' group refers to alkyl-CO— group, wherein alkyl group is as defined above. Acyl group refers to an alkyl-linker moiety bonded to the CO group. Examples of acyl groups include, but are not limited to, acetyl, propionyl and the like. Acyl group includes formyl group also.

As used herein, the expression 'aryl' means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "arylsulfonyl," is to be construed accordingly.

As used herein, the expression 'Cycloalkyl' group refers to a cyclic alkyl group which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms. Typical bridged cycloalkyl groups include, but are not limited to adamantyl, noradamantyl, bicyclo[1.1.0]butanyl, norbornyl(bicyclo[2.2.1]heptanyl), norbornenyl(bicyclo[2.2.1]heptanyl), norbornadienyl (bicyclo[2.2.1]heptadienyl), bicyclo[2.2.1]heptanyl, bicyclo [3.2.1]octanyl, bicyclo[3.2.1]octadienyl, bicyclo[2.2.2] octanyl, bicyclo[2.2.2]octenyl, bicyclo[2.2.2]octadienyl, bicyclo[5.2.0]nonanyl, bicyclo[4.3.2]undecanyl, tricyclo [5.3.1.1]dodecanyl and the like.

As used herein, the expression 'halogen or halo' represents fluorine, chlorine, bromine, or iodine.

As used herein, the expression 'haloalkyl' means at least one halogen atom is substituted on an alkyl group. Both halogen and alkyl have the meaning as defined above. Representative examples of haloalkyl groups include, but are not limited to, fluoromethyl, chloromethyl, fluoroethyl, chloroethyl, difluoromethyl, trifluoromethyl, dichloroethyl, trichloroethyl and the like. Unless otherwise specified, a haloalkyl group typically has from 1 to 10 carbon atoms.

As used herein, the expression 'haloalkoxy' means at least one halogen atom is substituted on an alkoxy group, wherein alkoxy and halogen groups are as defined above. Exemplary haloalkoxy groups include, but not limited to, fluoromethoxy, chloromethoxy, trifluoromethoxy, trichloroethoxy, fluoroethoxy, chloroethoxy, trifluoroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, a haloalkoxy group typically has from 1 to 10 carbon atoms.

As used herein, the expression 'heterocycle' or 'heterocyclyl' or 'heterocyclic' is a saturated monocyclic or polycyclic ring system of 3 to 10 members having at least one heteroatom or heterogroup selected from —O—, —N—, —S—, —SO$_2$, or —CO. Exemplary heterocyclyl groups include, but not limited to, azetidinyl, oxazolidinyl, oxazolidinonyl, isoxazolidinyl, imidazolidin-2-onyl, pyrrolidinyl, pyrrolidin-2-onyl, piperidinyl, piperazinyl, morpholinyl, thiomorpholinyl, thiomorpholine-1,1-dioxide, thiazolidinyl, 1,3-dioxolanyl, 1,4-dioxanyl, and the like. Unless otherwise specified, a heterocyclyl group typically has from 3 to about 10 carbon atoms.

As used herein, the expression 'heteroaryl' is an unsaturated, aromatic or non-aromatic, monocyclic or polycyclic ring system of 3 to 10 members having at least one heteroatom or heterogroup selected from —O—, —N—, —S—, —SO$_2$, or —CO. Exemplary heteroaryl groups include, but not limited to, oxazolyl, isoxazolyl, thiazolyl, pyridinyl, pyrrolyl, pyrimidinyl, thiazinyl, pyrazinyl, pyrazolyl, tetrazolyl, imidazothiazolyl, indolizidinyl, indolyl, quinolinyl, quinoxalinyl, benzoxazolyl, benzoisoxazolyl, benzothiazolyl, benzodioxolyl, benzotriazolyl, indazolyl, quinoxalinyl, imidazolyl, pyrazolopyridinyl, and the like. Unless otherwise specified, a heteroaryl group typically has from 3 to about 10 carbon atoms.

As used herein, the expression '5-7 membered heterocyclic or heteroaryl group' represents a heterocyclic or heteroaryl group as defined above having 5-7 ring atoms. Exemplary 5-7 membered heterocyclic or heteroaryl groups include, but not limited to, pyrazolyl, imidazolyl, isoxazolyl, oxazolyl, tetrazolyl, morpholinyl, oxazolidinonyl, and the like.

As used herein, the expression 'OH' represents a hydroxy group.

As used herein, the expression 'CN' represents a cyano group.

The cholesteryl ester-transfer protein (CETP) may be an animal or a non-mammalian or a mammalian protein, such as a human protein.

As used herein, the expression 'optionally substituted' means that the substitution is optional and therefore it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like.

As used herein and in the appended claims, the singular forms "a", "an", and "the" include plural reference unless the context clearly indicates otherwise.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

'Salts' refer to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the application. The preparation of salts can be carried out using known methods.

For example, pharmaceutically acceptable salts of compounds contemplated herein may be synthesized by conventional chemical methods using a parent compound containing either an acid or base functional group. Generally, such salts may be prepared, for example for compounds having the basic functional group, by reacting the free base with a stoichiometric quantity of the appropriate acid in the presence of a suitable solvent such as water or in an organic solvent, or in a mixture of the two. Generally, non-aqueous solvents such as ether, ethyl acetate, ethanol, isopropanol or acetonitrile may be utilized. Examples of acid addition salts include, but are not limited to, mineral acid addition salts such as hydrochloride, hydrobromide, hydroiodide, sulphate, nitrate, phosphate, and organic acid addition salts such as acetate, maleate, fumarate, citrate, oxalate, succinate, tartrate, malate, mandelate, methanesulphonate and p-toluenesulphonate. Also included in present application are the isomeric forms and tautomers and the pharmaceutically-acceptable salts of compounds of formula (I). Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids. Similarly, where the compounds carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts. In such situations the compound carrying an acidic moiety is reacted with suitable base such as an alkali, alkaline earth hydroxide or carbonate or organic amine in the presence of a suitable solvent such as water or organic solvents as described herein to prepare the alkali, alkaline earth metal or ammonium salt of the compound.

The term 'stereoisomers' is a general term used for all isomers of the individual molecules that differ only in the orientation of their atoms in space. Typically it includes mirror image isomers that are usually formed due to at least one asymmetric center (enantiomers). Where the compounds according to the present application possess one or more asymmetric centers and can thus occur as racemates, racemic mixtures, single enantiomers, diastereomeric mixtures and individual diastereomers. Also certain individual molecules may exist as geometric isomers (cis/trans). Similarly, certain compounds of this application may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such feasible isomers and mixtures thereof in any proportion are encompassed within the scope of the present application.

For any particular compound disclosed herein, any general structure presented also encompasses all conformational isomers, regioisomers and tautomers that may arise from a particular set of substituents.

As used herein, the term 'subject' or 'patient' means mammals, such as humans and other animals, including horses, dogs, cats, rats, mice, sheep, pigs, etc. In exemplary embodiments, the subject may include subjects for which treatment and/or prevention of the conditions described herein would be beneficial.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound that is effective in obtaining a desired clinical outcome in the treatment of a specific disease.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. Besides being useful for human treatment, these combinations are also useful for treatment of other mammals, including horses, dogs, cats, rats, mice, sheep, pigs, etc.

Terms such as "about," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

As used herein, "comprising" means the elements recited, or their equivalent in structure or function, plus any other element or elements which are not recited. The terms "having," "including," and "comprised of" are also to be construed as open ended unless the context suggests otherwise.

The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful or potentially useful in producing at least one physiological response in a subject to which such pharmaceutical composition is administered.

Reference will now be made in detail to the embodiments of the application, one or more examples of which are set forth below. Each example is provided by way of explanation of the present application, and not by way of limitation of the present application. In fact, it will be apparent to those skilled in the art that various modification and variations can be made in the present application without departing from the scope or spirit of the present application. For instance, features illustrated or described as part of one embodiment can be used on another embodiment to yield a still further embodiment. Thus it is intended that the present application cover such modifications and variations as come within the scope of the appended claims and their equivalents. Other objects, features, and aspects of the present application are disclosed in, or are obvious from, the following detailed description. It is to be understood by one of ordinary skill in the art that the present discussion is a description of exemplary embodiments only, and is not to be construed as limiting the broader aspects of the present application.

The present application provides a compound of formula (I), or stereoisomers thereof or pharmaceutically acceptable salts thereof:

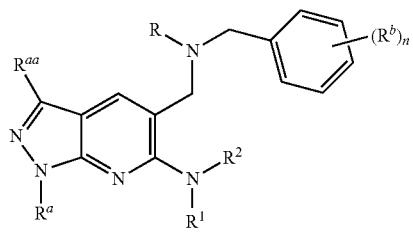
(I)

wherein,

R represents hydrogen or

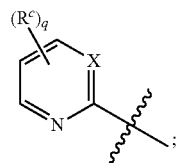

X represents —CH or —N;

R$^1$ and R$^2$ are independently of each other selected from hydrogen, acyl, alkyl or —(CH$_2$)$_p$-cycloalkyl;

R$^a$ and R$^{aa}$ are independently of each other selected from hydrogen or alkyl;

R$^b$, in each occurrence, is independently selected from halogen, alkyl, haloalkyl, hydroxy, alkoxy or haloalkoxy;

R$^c$, in each occurrence, is independently selected from hydrogen, cyano, halogen, alkyl, alkoxy, haloalkoxy, —COOR$^d$, —C(=O)—R$^e$, —CONR$^g$R$^h$, —C(=O)—CH=CH—NR$^i$R$^j$, —NHCOR$^f$, an optionally substituted group selected from cycloalkyl, aryl, heteroaryl or heterocycle ring, wherein the optional substituent, in each occurrence, is selected independently from hydrogen, halogen, cyano, hydroxyl, alkyl, haloalkyl, alkoxy, alkoxyalkyl or haloalkoxy;

R$^d$, R$^e$, R$^g$, R$^h$, R$^i$ and R$^j$, in each occurrence, independently of each other represents hydrogen or alkyl;

R$^f$ is selected from hydrogen, alkyl or cycloalkyl;

n is 0, 1, 2 or 3;

p is 0, 1, or 2; and q is 1 or 2.

In another embodiment, there is provided a compound of formula (Ia), or a stereoisomer thereof or a pharmaceutically acceptable salt thereof;

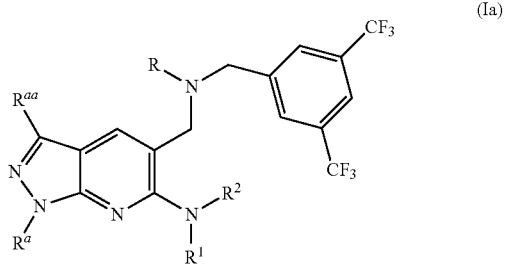
(Ia)

wherein,

R, R$^1$, R$^2$, R$^a$ and R$^{aa}$ are as defined above.

In another embodiment, the present application provides a compound of formula (Ib), or a stereoisomer thereof or a pharmaceutically acceptable salt thereof:

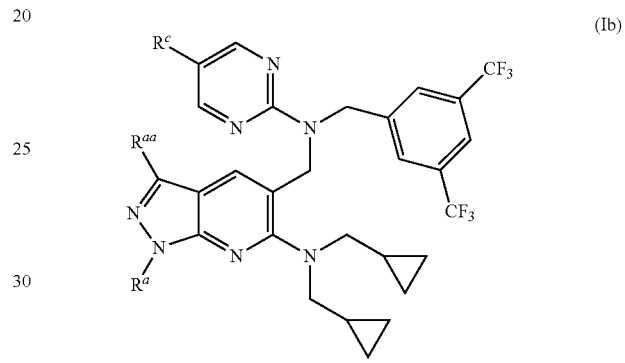
(Ib)

Wherein R$^a$, R$^{aa}$ and R$^c$ are as defined above.

In another embodiment, there is provided a compound of formula (Ic), or a stereoisomer thereof or a pharmaceutically acceptable salt thereof:

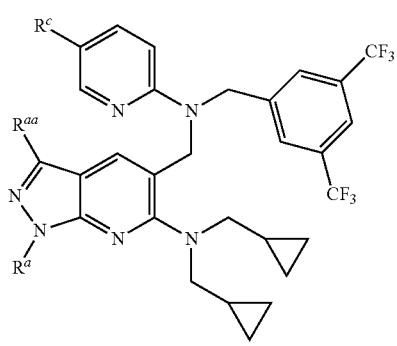
(Ic)

wherein, R$^a$, R$^{aa}$, and R$^c$ are as defined above.

In another embodiment there is provided a compound of formula (I), (Ia), (Ib) or (Ic), wherein R$^c$ represents a 5-7 membered heterocyclic or heteroaryl group.

In an embodiment, specific compounds of formula (I) without any limitation are enumerated as follows:

N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)isobutyramide, 5-(((3,5-bis(trifluoromethyl)benzyl)(5-cyclopropylpyridin-2-yl)amino)methyl)-1-(tert-butyl)-N,N-bis(cyclopropylmethyl)-3-methyl-1H-pyrazolo[3,4-b]pyridin-6-amine, N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)cyclopropane carboxamide, 1-(2-(((6-(bis(cyclopropylmethyl)amino)-1,3-dimethyl-1H-pyrazolo[3,4-b]pyridin-5-yl)methyl)(3,5-bis(trifluoromethyl)benzyl)amino)pyrimidin-5-yl)ethanone, 1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)ethanone, (E)-1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)-3-(dimethylamino)prop-2-en-1-one, 5-(((3,5-bis(trifluoromethyl)benzyl)(5-(isoxazol-3-yl)pyrimidin-2-yl)amino)methyl)-N,N-bis(cyclopropylmethyl)-1,3-dimethyl-1H-pyrazolo[3,4-b]pyridin-6-amine, 5-(((5-(1H-pyrazol-3-yl)pyrimidin-2-yl)(3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine, 5(((3,5-bis(trifluoromethyl)benzyl)(5-(1-methyl-1H-pyrazol-3-yl)pyrimidin-2-yl)amino)methyl)-1-(tert-butyl)-N,N-bis(cyclopropylmethyl)-3-methyl-1H-pyrazolo[3,4-b]pyridin-6-amine, 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carbonitrile, 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxamide, 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-N,N-dimethylpyrimidine-5-carboxamide, 3-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)oxazolidin-2-one, 5(((3,5-bis(trifluoromethyl)benzyl)(5-morpholinopyrimidin-2-yl)amino)methyl)-1-(tert-butyl)-N,N-bis(cyclopropylmethyl)-3-methyl-1H-pyrazolo[3,4-b]pyridin-6-amine, 5(((3,5-bis(trifluoromethyl)benzyl)(5-morpholinopyrimidin-2-yl)amino)methyl)-N,N-bis(cyclopropylmethyl)-1,3-dimethyl-1H-pyrazolo[3,4-b]pyridin-6-amine, 1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)pyrrolidin-2-one, Ethyl-2(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-4-methylpyrimidine-5-carboxylate, 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-4-methylpyrimidine-5-carboxylic acid, Ethyl-2(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxylate, 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxylic acid, 5-(((3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine, and 5-(((3,5-bis(trifluoromethyl)benzyl)(5-bromopyrimidin-2-yl)amino) methyl)-1-(tert-butyl)-N,N-bis(cyclopropylmethyl)-3-methyl-1H-pyrazolo[3,4-b]pyridin-6-amine, or stereoisomers thereof or pharmaceutically acceptable salts thereof.

The compounds of formula (I) may exist in the form of pharmaceutically acceptable salts. Such pharmaceutically acceptable salts are also a part of this application.

The compounds of formula (I) may exist in the form of stereoisomers. Such stereoisomers are also a part of this application.

The compounds of formula (I) may also exist in the form of stereoisomers and/or their pharmaceutically acceptable salts. Such stereoisomers and/or their pharmaceutically acceptable salts are part of this application.

In another embodiment, the present application provides a pharmaceutical composition comprising a pharmaceutically acceptable carrier and a therapeutically effective amount of one or more compounds of formula (I) or a stereoisomer thereof or a pharmaceutically acceptable salt thereof.

In another embodiment, there is provided compounds of formula (I) or stereoisomers thereof or pharmaceutically acceptable salt thereof, as CETP inhibitors.

In another embodiment, there is provided a method of administering CETP inhibitors in a subject (i.e., a patient), which comprises administering to said subject (i.e., a patient) a pharmaceutical composition comprising a therapeutically effective amount of a compound of formula (I) or a stereoisomer thereof or a pharmaceutically acceptable salt thereof. As used herein the term "subject" and "patient" can be the same and can be used interchangeably.

In another embodiment, there is provided a method of increasing the level of HDL cholesterol and/or a decreasing the level of very low density lipoprotein (VLDL) and low density lipoprotein (LDL) and/or increasing the ratio of HDL-C to LDL-C, which comprises administering to said subject a pharmaceutical composition comprising an effective amount of a compound of formula (I) or a stereoisomer thereof or a pharmaceutically acceptable salt thereof.

In another embodiment, there is provided a method for treating or reducing the risk of developing a disease or condition that may be treated or prevented by inhibition of CETP in a patient in need of such a treatment comprising the administration of a therapeutically effective amount of a compound of formula (I) or a stereoisomer thereof or a pharmaceutically acceptable salt thereof to said patient.

In another embodiment, there is provided a method of binding CETP in a patient in need of such a treatment comprising the administration of a therapeutically effective amount of the compound of formula (I), or a stereoisomer thereof or a pharmaceutically acceptable salt thereof to said patient.

In another embodiment, there is provided a method of increasing the level of HDL cholesterol in a patient in need of such a treatment comprising the administration of a therapeutically effective amount of the compound of formula (I), or a stereoisomer thereof or a pharmaceutically acceptable salt thereof to said patient.

In another embodiment, there is provided a method of lowering LDL cholesterol in a patient in need of such a treatment comprising the administration of a therapeutically effective amount of the compound of formula (I), or a stereoisomer thereof or a pharmaceutically acceptable salt thereof to said patient.

In another embodiment, there is provided a method of raising the ratio of increasing HDL cholesterol to LDL cholesterol in a patient in need of such a treatment comprising the administration of a therapeutically effective amount of the compound of the formula (I), or a stereoisomer thereof or a pharmaceutically acceptable salt thereof to said patient.

In another embodiment, there is provided a method of treating or preventing atherosclerosis in a patient in need of such a treatment comprising the administration of a therapeutically effective amount of the compound of formula (I), or a stereoisomer thereof or a pharmaceutically acceptable salt thereof to said patient.

The pharmaceutical composition of a compound of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present application may be administered in a wide variety of different dosage forms. For example, they may be combined with various pharmaceutically acceptable inert carriers in the form of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include solid diluents or fillers, sterile aqueous media, and various nontoxic organic solvents, etc. Moreover, oral pharmaceutical compositions may be sweetened and/or flavored. In general, the compounds of the present application may be present in such dosage forms at concentration levels ranging from about 0.1% to about 90% by weight.

In general, compounds of the present application for treatment may be administered to a subject in a suitable effective dose in the range of from about 0.01 to about 100 mg per kilogram of body weight of recipient per day, in some embodiments, in the range of from about 0.5 to about 50 mg per kilogram body weight of recipient per day, in still other embodiments, in the range of from about 0.1 to about 20 mg per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present application provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present application claimed herein. All temperatures are in degrees Celsius (° C.) unless otherwise noted.

The following acronyms, abbreviations, terms and definitions have been used throughout the reaction scheme and experimental section.

$CDCl_3$ (deuterated chloroform), $Cs_2CO_3$ (cesium carbonate), CuI (cuprous iodide), CuCN (copper(I) cyanide), DCM (dichloromethane), DMF (N,N-dimethylformamide), DMF-DMA (N,N-dimethylformamide-dimethyl acetal), DME (dimethoxyethane), DMSO (dimethyl sulfoxide), EtOH (ethanol), EtOAC (ethyl acetate), HCl (hydrochloric acid), MeOH (methanol), $K_2CO_3$ (potassium carbonate), KOH (potassium hydroxide), $KOBu^t$ (potassium tert-butoxide), KCN (potassium cyanide), $K_3PO_4$ (tripotassium phosphate), LiOH (lithium hydroxide), Pd (palladium), $Pd(OAc)_2$ (palladium (II) acetate), $Pd_2(dba)_3$ (tris(dibenzylideneacetone)dipalladium(0)), $NaHCO_3$ (sodium bicarbonate), $Na_2CO_3$ (sodium carbonate), NaCN (sodium cyanide), NaOH (sodium hydroxide), $Na(CN)BH_3$ (sodium cyanoborohydride), NaOtBu (sodium tert-butoxide), NaH (sodium hydride), $Na_2SO_4$ (sodium sulfate), $NaBH_4$ (sodium borohydride), $Na(OAc)_3BH$ (sodium triacetoxyborohydride), $Ti(i-Pro)_4$ (titanium(IV) isopropoxide), THF (tetrahydrofuran), $Zn(CN)_2$ (zinc cyanide), EDTA (Ethylenediaminetetraacetic acid), h (hour), min (minute), MS (mass spectroscopy), NMR (nuclear magnetic resonance), Mp/mp (melting point), aq (aqueous), ° C. (degree Celsius), psi (pounds per square inch).

NMR abbreviations: MHz (Megahertz), s (singlet), d (doublet), t (triplet), q (quartet), dd (doublet of doublets), m (multiplet), bs (broad singlet).

Another embodiment of the present application provides a process for the preparation of compounds of formulae (11), (12), (13), (14), (15) & (16) which represent a sub-group of a compound of formula (I), wherein all symbols/variables are as defined earlier unless otherwise stated. The process is represented by Scheme-1:

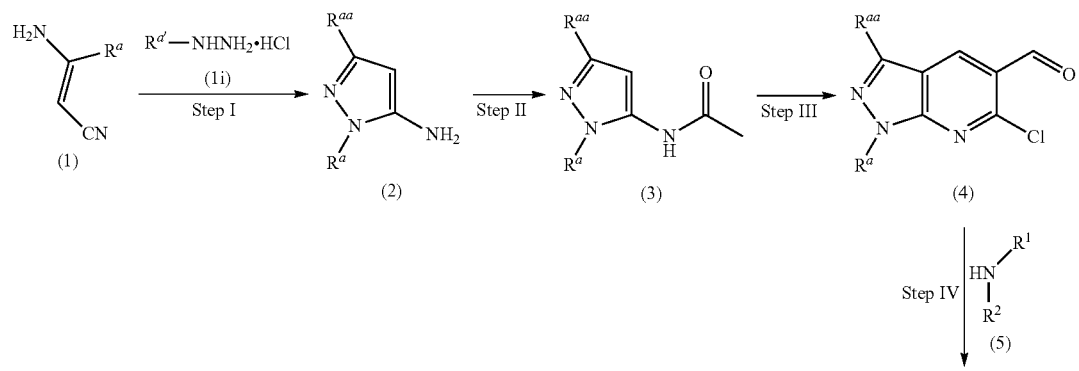

-continued
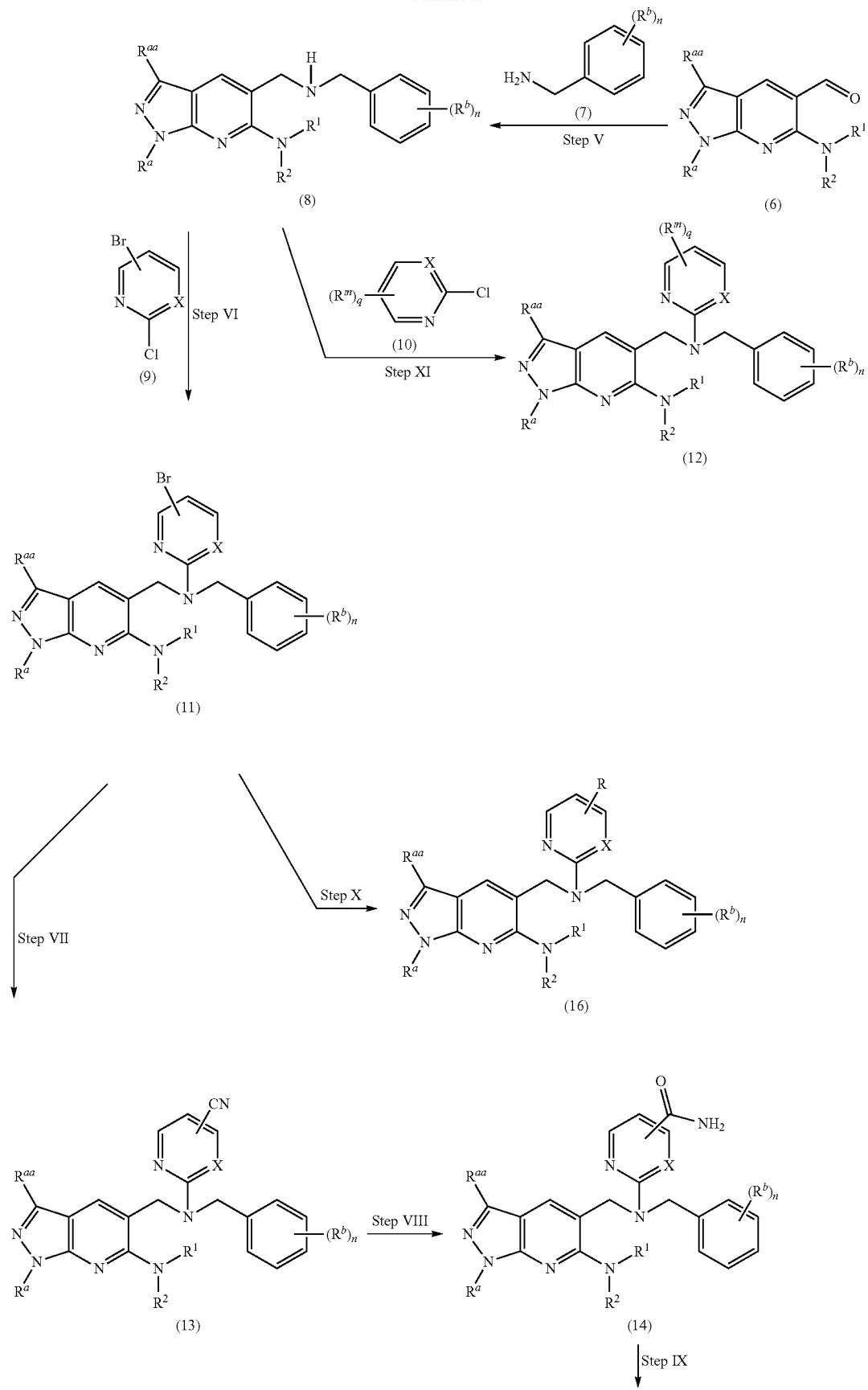

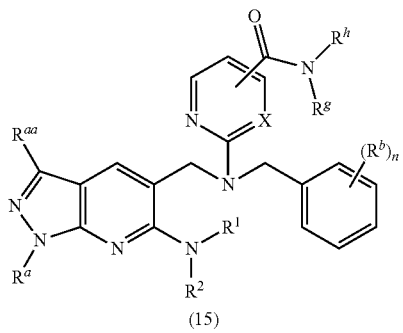

(15)

Step I

A compound of formula (2) can be obtained by reacting an α,β-unsaturated nitrile of formula (1) with a substituted hydrazine of formula (1i) in presence of a base such as triethylamine, $K_2CO_3$, $Cs_2CO_3$ and the like in a suitable solvent such as methanol, ethanol, THF, DMF and the like. $R^a$ and $R^{aa}$ independently represent an alkyl group.

Step II

An amine compound of formula (2) can be reacted with acetylating agent such as acetic anhydride, acetyl chloride, at a temperature of about 20-35° C. for a sufficient duration, which can range from about 1 to 2 h or more to obtain a compound of formula (3).

Step III

A compound of formula (3) can be treated with a suitable reagent such as phosphoryl trichloride, thionyl chloride, phosphorous pentachloride and the like in a suitable solvent, e.g., DMF, DME, DMSO to obtain a compound of formula (4).

Step IV

A compound of formula (4) can be reacted with an amine of formula (5) in presence of a base such as $K_2CO_3$, $NaHCO_3$, $Na_2CO_3$, $Cs_2CO_3$, $KOBu^t$ and the like, in a solvent such as toluene, DMF, DMSO, acetonitrile, t-butanol and the like to obtain a compound of formula (6), wherein $R^1$ and $R^2$ are as defined in formula (I).

Step V

Reductive amination of compound of formula (6) with a compound of formula (7) can be carried out for example in presence of a reducing agent such as $Na(CN)BH_3$, $Na(OAc)_3BH$, $NaBH_4$, $Ti(i-PrO)_4$, pyridine-borane complex and the like, in a $(C_1-C_{10})$ alcohol solvent such as methanol, ethanol, propanol, isopropanol, and the like, or a chlorinated solvent such as dichloromethane, chloroform, 1,2-dichloroethane, and the like, along with an acid such as acetic acid or diluted hydrochloric acid. The temperature of the reaction could be maintained from about 25° C. to about 35° C., and the duration of the reaction typically could range from about 30 minutes to about 5 hours. $R^a$, $R^{aa}$, $R^1$, $R^2$, $R^b$ and n are as defined in formula (I).

Step VI

A compound of formula (11) can be obtained by reacting a compound of formula (8) with a compound of formula (9) in presence of a base such as potassium carbonate, sodium carbonate, potassium acetate, cesium carbonate, triethylamine, disiopropylethylamine and the like, in a solvent such as anhydrous DMF, 1,4-dioxane, DMSO, acetonitrile, and the like, under suitable reaction conditions.

Step VII

A compound of formula (13) can be obtained by cyanation of a compound of formula (11) using a suitable cyanating agent such as CuCN, $Zn(CN)_2$, NaCN, KCN and the like in a solvent such as DMF, toluene, DMSO, and the like, under suitable reaction conditions.

Step VIII

Base catalyzed hydrolysis of the cyano group in the compound of formula (13) in presence of a base such as KOH, NaOH, LiOH and the like in a solvent such as ethanol, methanol, n-butanol, tert-butanol and the like can yield a carboxamide of formula (14).

Step IX

A compound of formula (15) can be obtained by N-alkylation of the alkali salt of the carboxamide compound of formula (14). The carboxamide compound can be converted to its salt using metallic sodium, NaH, $K_2CO_3$ and the like. N-alkylation can be done by using alkylating agents such as alkyl halide and the like under suitable reaction conditions. $R^g$ and $R^h$ are as defined in the description of formula (I).

Step X

A compound of formula (16) can be obtained by performing various substitution reactions on the compound of formula (11) wherein R represents halogen, alkyl, alkoxy, haloalkoxy, —$NHCOR^t$ and the like, wherein $R^t$ is as defined in compound of formula (I).

Step XI

A compound of formula (12) can be obtained by reacting a compound of formula (8) with a compound of formula (10) in the presence of a base such as $K_2CO_3$, $Na_2CO_3$, $Cs_2CO_3$ and the like under suitable reaction conditions. X, $R^a$, $R^{aa}$, $R^1$, $R^2$, $R^b$, q and n are as defined herein for the compound of formula (I).

Another embodiment of the present application provides a process for the preparation of various compounds from compound of formula (12), wherein all symbols/variables are as defined earlier unless otherwise stated. The process is represented by Scheme-II:

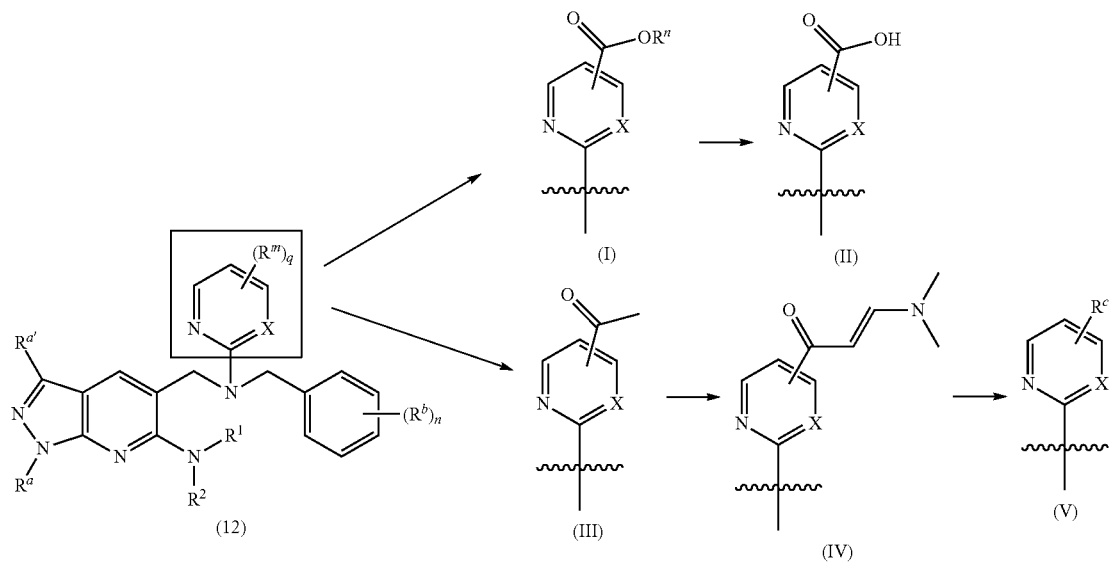

Various substituents of R<sup>m</sup> containing compounds of formula (12) can be prepared either by using a suitable precursor compound of formula (12) in step XI or by further fictionalization of

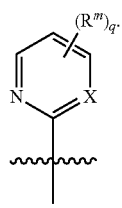

For example a compound of formula (12) with R<sup>m</sup> as an acetyl group (III) or an ester group (I) can be obtained by using precursors having the respective substitutions. The ester group can be further hydrolysed for example by a base or acid catalyzed hydrolysis, to obtain a carboxyl group (II). Also when R<sup>m</sup> is an acetyl group, it could further be converted to a group as shown in (IV) by reacting it with a suitable reagent such as DMF-DMA and the like. This 3-dimethylamino-prop-2-enonyl moiety can be further converted to R<sup>c</sup> (V), wherein R<sup>c</sup> represents a heterocycle, heteroaryl group; by reacting it with suitable reagents known in the art. For example, reaction with hydroxylamine hydrochloride under suitable reaction conditions would yield an isoxazolyl group. Reaction with hydrazine hydrate would yield pyrazolyl moiety. Such heterocycles and heteroaryl groups could be further substituted by groups such as alkyl, halogen, cyano, hydroxyl, haloalkyl, alkoxy, alkoxyalkyl, haloalkoxy and the like using suitable reagents and synthetic methods known in the art.

EXAMPLES

Example 1

N-(2-(((6-(bis(cyclopropylmethyl)amino)-1-(tert-butyl)-3-methyl-1H-pyrazolo[3,4-b]pyridin-5-yl) methyl)(3,5-bis(trifluoromethyl)benzyl)amino)pyrimidin-5-yl) isobutyramide

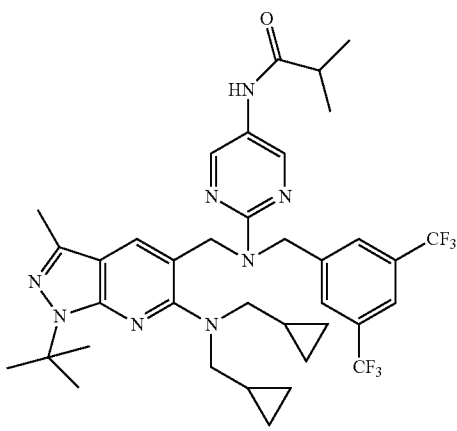 [SMILES: Cc1nn(C(C)(C)C)c2nc(N(CC3CC3)CC3CC3)c(CN(Cc3cc(C(F)(F)F)cc(C(F)(F)F)c3)c3ncc(NC(=O)C(C)C)cn3)cc12]

Step (i): Preparation of 1-(tert-Butyl)-3-methyl-1H-pyrazol-5-amine

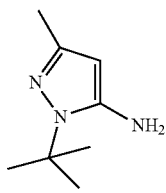

To a mixture of 3-aminobut-2-enenitrile (60 g, 731 mmol) and tert-butylhydrazine (96 g, 731.1 mmol) in ethanol (35 ml), triethylamine (220 ml, 2195 mmol) was added. The mixture was refluxed for 12-16 h. The reaction mixture was then concentrated under reduced pressure. The concentrate was extracted with water (100 ml) and ethylacetate (700 ml). The organic layer was washed with brine and dried over $Na_2SO_4$ and concentrated under reduced pressure to obtain the title product.

$^1$H NMR (400 MHz, $CDCl_3$) δ 5.37 (s, 1H), 3.51 (bs, 2H), 2.14 (s, 3H), 1.61 (s, 9H).
MS (m/z): 154 ($M^+$+1, 100%).

Step (ii): Preparation of N-(1-(tert-Butyl)-3-methyl-1H-pyrazol-5-yl)acetamide

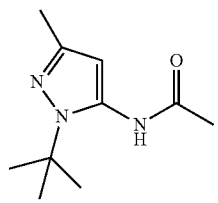

To 1-(tert-butyl)-3-methyl-1H-pyrazol-5-amine (110 g, 0.71 mol), acetic anhydride (73 ml, 0.71 mol) was added dropwise with stirring. The reaction mixture was stirred for 1-2 h at 20-35° C. Thereafter the reaction mixture was washed with excess of hexane and filtered to obtain the title compound as a yellow solid. MP: 118-120° C.

$^1$H NMR (400 MHz, $CDCl_3$) δ 7.27, (bs, 1H), 6.003 (s, 1H), 2.17 (s, 3H), 1.62 (s, 9H).
MS (m/z): 196 ($M^+$+1, 70%).

Step (iii): Preparation of 1-(tert-Butyl)-6-chloro-3-methyl-1H-pyrazolo[3,4-b]pyridine-5-carbaldehyde

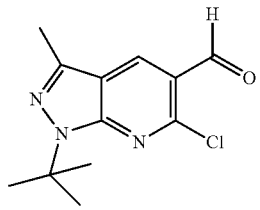 [SMILES: Cc1nn(C(C)(C)C)c2nc(Cl)c(C=O)cc12]

Phosphorus oxychloride (62 g, 407 mmol) was added to 1-(tert-butyl)-6-chloro-3-methyl-1H-pyrazolo[3,4-b]pyridine-5-carbaldehyde (15 g, 8.8 mmol) and the mixture was heated while stirring at 90-95° C. for 3 h. Thereafter, anhydrous DMF (18 g, 246 mmol) was added slowly over the period of 30 min while maintaining the temperature of the mixture at 90-95° C. After stirring for an additional 2 h, the reaction mixture was cooled to 20-35° C. and poured over crushed ice (100 g). The precipitated solid was filtered off, washed with water and dried under reduced pressure.

The yellowish solid product was subsequently dissolved in methylene chloride (200 mL), washed with water, dried over sodium sulfate, and the solvent was evaporated under reduced pressure to give the desired product as a light yellow solid.
MS (m/z): 251 ($M^+$+1).

Step (iv): Preparation of 6-(Bis(cyclopropylmethyl)amino)-1-(tert-butyl)-3-methyl-1H-pyrazolo[3,4-b]pyridine-5-carbaldehyde

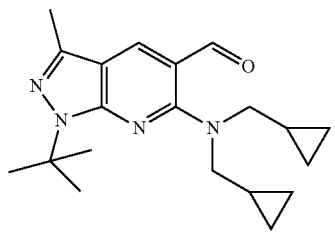 [SMILES: Cc1nn(C(C)(C)C)c2nc(N(CC3CC3)CC3CC3)c(C=O)cc12]

Potassium carbonate (8.2 g, 57 mmol) was added to a solution of 1-(tert-butyl)-6-chloro-3-methyl-1H-pyrazolo[3,4-b]pyridine-5-carbaldehyde (5 g, 29 mmol) and bis-cyclopropylmethyl amine-(3.7 ml, 1.5 mmol) (prepared following the literature method disclosed in U.S. Pat. No. 3,546,295) in DMSO (50 mL) under nitrogen. After stirring for 0.5 h at 20-35° C., the reaction mixture was heated for 14 h at 80° C.

Thereafter, the reaction was cooled to 20-35° C., water (30 mL) and ethyl acetate (30 mL) were added, and the organic layer was separated from the mixture. The organic extract was washed with brine, dried over sodium sulfate and the solvent was removed using a rotary evaporator under vacuum. The residue was purified by chromatography using silica gel (60-120 mesh) and eluted with 5% eluent to afford the title compound as a yellow solid.
MS (m/z): 341 ($M^+$+1, 100%).

Step (v): Preparation of 5-(((3,5-Bis(trifluoromethyl)benzyl)amino)methyl)-1-(tert-butyl)-N,N-bis(cyclopropylmethyl)-3-methyl-1H-pyrazolo[3,4-b]pyridin-6-amine

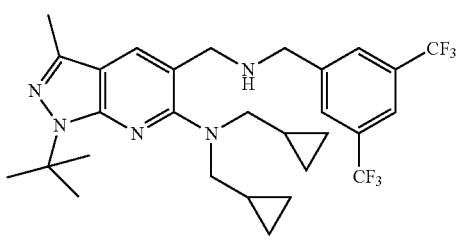 [SMILES: Cc1nn(C(C)(C)C)c2nc(N(CC3CC3)CC3CC3)c(CNCc3cc(C(F)(F)F)cc(C(F)(F)F)c3)cc12]

Acetic acid (2.82 g, 46 mmol) was added to a mixture of 6-(bis(cyclopropylmethyl)amino)-1-(tert-butyl)-3-methyl-1H-pyrazolo[3,4-b]pyridine-5-carbaldehyde (8 g, 23 mmol)

and (3,5-bis(trifluoromethyl)phenyl)methanamine (5.7 g, 23 mmol) in methanol at 0° C. The resulting mixture was stirred continuously for 20 min. Sodium cyanoborohydride (4.5 g, 70 mmol) was added portion wise to the reaction mixture at 0° C. and the mixture was stirred for 1 h. After which the mixture was quenched with water, organic layer was separated, washed with brine, dried and evaporated to obtain the title compound.

$^1$H NMR (400 MHz, CDCl$_3$) δ 7.71-7.81 (m, 4H), 3.91 (s, 2H), 3.83 (s, 2H), 3.11-3.13 (m, 4H), 2.49 (s, 3H), 1.76 (s, 9H), 0.9-0.95 (m, 2H), 0.33-0.37 (m, 4H), 0.008-0.07 (m, 4H);

MS (m/z): 568 (M$^+$+1, 100%).

Step (vi): Preparation of 5-(((3,5-Bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine

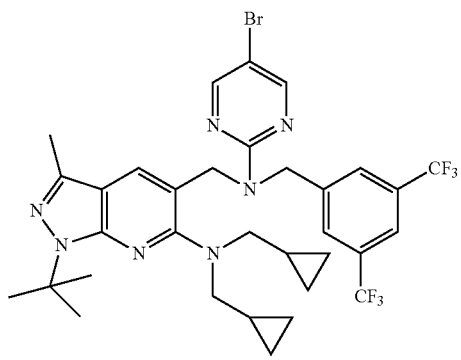 [SMILES: Cc1nn(C(C)(C)C)c2nc(N(CC3CC3)CC3CC3)c(CN(Cc3cc(C(F)(F)F)cc(C(F)(F)F)c3)c3ncc(Br)cn3)cc12]

Potassium carbonate (0.43 g, 3 mmol) was added to a mixture of 5-(((3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine (0.6 g, 1 mmol) and 5-bromo-2-chloropyrimidine (0.6 g, 3 mmol) in DMF. The resultant mixture was stirred at 100° C. for 12-16 h. The reaction mixture was treated with water and extracted with ethylacetate (100 ml). The organic layer was washed with brine and dried over Na$_2$SO$_4$, concentrated under reduced pressure to obtain the crude product. This product was further purified by column chromatography using silica gel (60-120 mesh) and 5% ethyl acetate in petroleum ether as eluent.

$^1$H NMR (400 MHz, CDCl$_3$) δ 8.69 (s, 2H), 7.69-7.72 (m, 3H), 5.035 (s, 2H), 4.80 (s, 2H), 3.07-3.15 (m, 4H), 2.40 (s, 3H), 1.79 (s, 9H), 0.89-0.86(m, 2H), 0.31-0.36 (m, 4H), 0.015-0.07 (m, 4H)

MS (m/z): 726 (M$^+$+1, 30%).

Step (vii): Preparation of N-(2-((((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl) isobutyramide 5-(((3,5-Bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine (150 mg, 0.207 mmol) and isobutyramide (0.018 g, 0.207 mmol) were dissolved in 1,4-dioxane (5 ml) in a sealed tube to which 1,2-transdiaminocyclohexane (0.007 g, 0.062 mmol), and CuI (0.007 g, 0.078 mmol) were added. The reaction mixture was de-gassed for 15 min with argon. K$_2$CO$_3$ (0.057 g, 0.414 mmol) was added to the reaction mixture and it was further degassed with argon for 15 min. The reaction mixture was then stirred at 80° C. for 3 days. Thereafter the reaction mixture was diluted with DCM-MeOH (3:1) mixture (10 ml), filtered through celite. The filtrate was concentrated under reduced pressure; purified by column chromatography using 60-120 silica gel and 25% EtOAc in petroleum ether as the eluent to obtain the title compound.

$^1$H NMR (400 MHz, CDCl$_3$) δ 8.53 (s, 2H), 7.75 (s, 3H), 7.70 (s, 1H), 6.91 (s, 1H), 5.05 (s, 2H), 4.82 (s, 2H), 3.09 (d, J=6.8 Hz, 4H), 2.39 (s, 3H), 1.78 (s, 9H), 1.28 (d, J=6.8 Hz, 6H), 0.92-0.88 (m, 3H), 0.84 (q, J=1.6 Hz, 4H), 0.07-0.008 (m, 4H). MS (m/z): 731 (M$^+$+1, 100%).

Example 2

5-(((3,5-Bis(trifluoromethyl)benzyl)(5-cyclopropylpyridin-2-yl)amino)methyl)-1-(tert-butyl)-N,N-bis(cyclopropylmethyl)-3-methyl-1H-pyrazolo[3,4-b]pyridin-6-amine

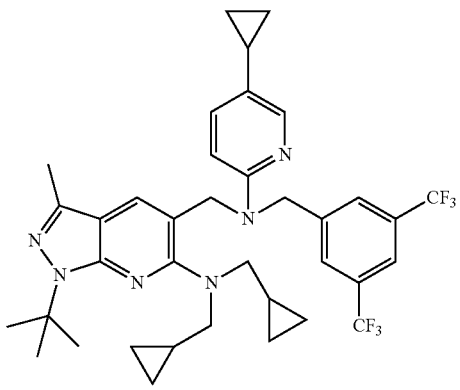 [SMILES: Cc1nn(C(C)(C)C)c2nc(N(CC3CC3)CC3CC3)c(CN(Cc3cc(C(F)(F)F)cc(C(F)(F)F)c3)c3ccc(C4CC4)cn3)cc12]

Step (i): Preparation of 5-(((3,5-Bis(trifluoromethyl)benzyl)(5-bromopyridin-2-yl)amino) methyl)-1-(tert-butyl)-N,N-bis(cyclopropylmethyl)-3-methyl-1H-pyrazolo[3,4-b]pyridin-6-amine

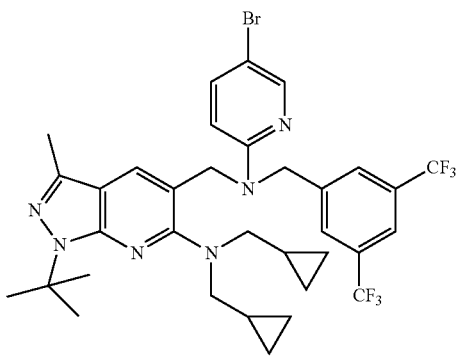 [SMILES: Cc1nn(C(C)(C)C)c2nc(N(CC3CC3)CC3CC3)c(CN(Cc3cc(C(F)(F)F)cc(C(F)(F)F)c3)c3ccc(Br)cn3)cc12]

The title compound was prepared by following the procedures substantially same as set forth in step (vi) of Example-1, and by employing appropriate starting materials.

Step (ii): Preparation of 5-(((3,5-Bis(trifluoromethyl)benzyl)(5-cyclopropylpyridin-2-yl)amino)methyl)-1-(tert-butyl)-N,N-bis(cyclopropylmethyl)-3-methyl-1H-pyrazolo[3,4-b]pyridin-6-amine 5-(((3,5-bis(trifluoromethyl)benzyl)(5-bromopyridin-2-yl)amino)methyl)-1-(tert-butyl)-N,N-bis(cyclopropylmethyl)-3-methyl-1H-pyrazolo[3,4-b]pyridin-6-amine (0.05 g, 0.069 mmol) as prepared above, cyclopropyl boronic acid (0.007 g, 0.083 mmol) were dissolved in toluene (10 ml). To this tricyclohexylphosphine (0.002 g, 0.0069 mmol), Pd(OAc)$_2$ (0.0007 g, 0.0034 mmol), K$_3$PO$_4$ (0.051 g, 0.241 mmol) were added. The mixture was stirred at 100° C. for 16 hr. The reaction mixture was diluted with water, extracted with EtOAc. The combined organic layer was washed with brine, dried over Na$_2$SO$_4$, and concentrated under reduced pressure. The crude product thus obtained, was purified by column chromatography using silica gel 60-120 mesh, 10% EtOAc in petroleum ether as the eluent to obtain the title compound.

$^1$H NMR (400 MHz, CDCl$_3$) δ 8.20 (s, 2H), 7.69 (m, 3H), 7.60 (s, 1H), 5.03 (s, 2H), 4.81 (s, 2H), 3.09-3.07 (m, 4H), 2.38 (s, 3H), 1.77 (s, 9H), 0.96-0.91 (m, 4H), 0.66-0.65 (m, 2H), 0.008-0.003 (m, 8H). MS (m/z): 686 (M$^+$+1, 100%).

Example 3

N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)cyclopropanecarboxamide

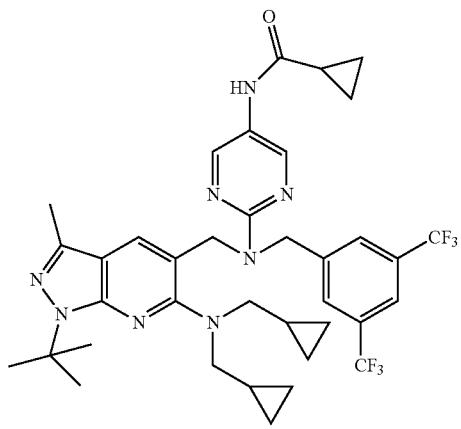 [SMILES: Cc1nn(C(C)(C)C)c2nc(N(CC3CC3)CC3CC3)c(CN(Cc3cc(C(F)(F)F)cc(C(F)(F)F)c3)c3ncc(NC(=O)C4CC4)cn3)cc12]

The title compound was synthesized using procedures substantially same as set forth in Example 1 and by using cyclopropane amide instead of isobutyramide in step (vii).

$^1$H NMR (400 MHz, CDCl$_3$) δ 8.53 (s, 2H), 7.70 (s, 3H), 7.62 (s, 1H), 5.05 (s, 2H), 4.81 (s, 2H), 3.08 (d, J=6.8 Hz, 4H), 2.39 (s, 3H), 1.78 (s, 9H), 1.57-0.88 (m, 6H), 0.33 (q, J=1.6 Hz, 4H), 0.027-0.001 (m, 4H). MS (m/z): 729 (M$^+$+1, 100%).

Example 4

1-(2-(((6-(bis(cyclopropylmethyl)amino)-1,3-dimethyl-1H-pyrazolo[3,4-b]pyridin-5-yl)methyl)(3,5-bis(trifluoromethyl)benzyl)amino)pyrimidin-5-yl)ethanone

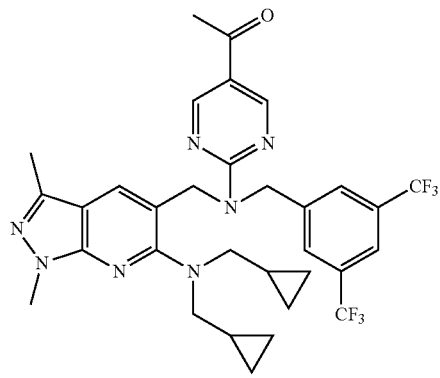 [SMILES: CC(=O)c1cnc(N(Cc2cc(C(F)(F)F)cc(C(F)(F)F)c2)Cc2cc3c(C)nn(C)c3nc2N(CC2CC2)CC2CC2)nc1]

Step (i): Preparation of 5(((3,5-bis(trifluoromethyl)benzyl)amino)methyl)-N,N-bis(cyclopropylmethyl)-1,3-dimethyl-1H-pyrazolo[3,4-b]pyridin-6-amine

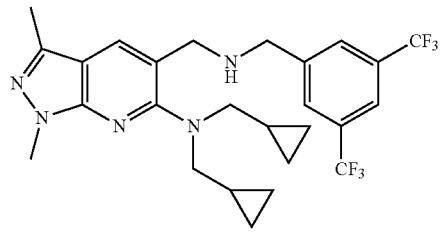 [SMILES: Cc1nn(C)c2nc(N(CC3CC3)CC3CC3)c(CNCc3cc(C(F)(F)F)cc(C(F)(F)F)c3)cc12]

The title compound was synthesized using procedures substantially same as set forth in step (v) of Example 1 and using appropriate starting materials.

Step (ii): Preparation of 1-(2-(((6-(bis(cyclopropylmethyl)amino)-1,3-dimethyl-1H-pyrazolo[3,4-b]pyridin-5-yl)methyl)(3,5-bis(trifluoromethyl)benzyl)amino)pyrimidin-5-yl)ethanone 5-(((3,5-bis(trifluoromethyl)benzyl)amino)methyl)-N,N-bis(cyclopropylmethyl)-1,3-dimethyl-1H-pyrazolo[3,4-b]pyridin-6-amine (0.761 mmol, 0.400 g) in DMF was treated with 1-(2-chloropyrimidin-5-yl)ethanone (0.761 mmol, 0.119 g) and K$_2$CO$_3$ (2.283 mmol, 0.315 g). The reaction mixture was stirred at 60-70° C. for 12-16 h. The reaction mixture was then extracted with EtOAc. The combined organic layer was washed with water and brine solution, dried over sodium sulphate, concentrated under reduced pressure and purified by column chromatography using silica gel and 50% EtOAc in petroleum ether as eluent to get the title compound.

$^1$H NMR (400 MHz, CDCl$_3$) δ 8.9 (s, 1H), 7.70 (s, 1H), 7.60 (s, 2H), 7.50 (s, 1H), 5.10 (s, 2H), 4.80 (s, 2H), 3.90 (s,

3H), 3.10 (d, J=6.0 Hz, 4H), 2.50 (s, 3H), 2.30 (s, 3H), 0.90 (m, 2H), 0.40 (m, 4H), 0.10 (m, 4H). MS (m/z): 646 (M⁺+1, 50%).

Example 5

1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)ethanone

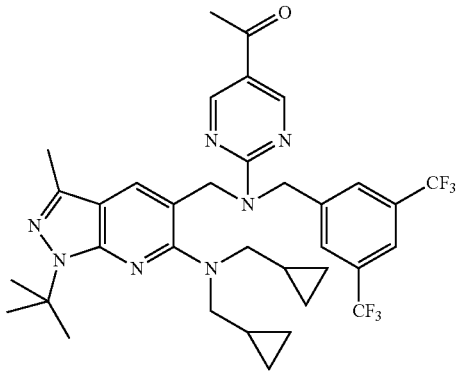 [SMILES: CC(=O)c1cnc(N(Cc2cc(C(F)(F)F)cc(C(F)(F)F)c2)Cc2cc3c(C)nn(C(C)(C)C)c3nc2N(CC2CC2)CC2CC2)nc1]

The title compound was obtained following the procedures substantially same as set forth in Example 4 and using 5-(((3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine, obtained in step (v) of Example 1 as a starting material.

¹H NMR (400 MHz, CDCl₃) δ 8.90 (d, 2H), 7.80 (m, 3H), 7.60 (s, 1H), 5.10 (s, 2H), 4.90 (s, 2H), 3.10 (d, J=6.0 Hz, 4H), 2.54 (s, 3H), 2.39 (s, 3H), 1.20 (s, 9H), 0.30 (m, 4H), 0.01 (m, 4H). MS (m/z): 688 (M⁺+1, 100%).

Example 6

(E)-1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)-3-(dimethyl amino)prop-2-en-1-one

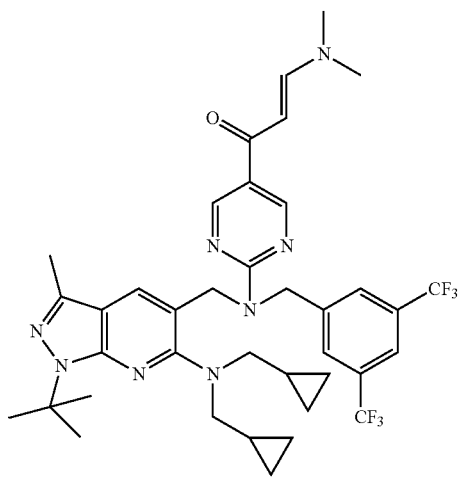 [SMILES: Cc1nn(C(C)(C)C)c2nc(N(CC3CC3)CC3CC3)c(CN(Cc3cc(C(F)(F)F)cc(C(F)(F)F)c3)c3ncc(C(=O)/C=C/N(C)C)cn3)cc12]

1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)ethanone, obtained in Example 5, (0.1 g, 0.14 mmol) and DMF-DMA (0.02 mL) was taken in toluene (2 mL) and refluxed the reaction mixture for 48 h. Water was added to the cooled (to 20-35° C.) reaction mass and was extracted it with ethyl acetate. The organic layer was dried over sodium sulfate, solvent was evaporated to get the crude product which was purified by column chromatography using 60-120 mesh silica gel and eluted the desired product with 20% ethyl acetate in petroleum ether. MS (m/z): 743 (M⁺+1, 100%).

Example 7

5-(((3,5-Bis(trifluoromethyl)benzyl)(5-(isoxazol-3-yl)pyrimidin-2-yl)amino)methyl)-N,N-bis(cyclopropylmethyl)-1,3-dimethyl-1H-pyrazolo[3,4-b]pyridin-6-amine

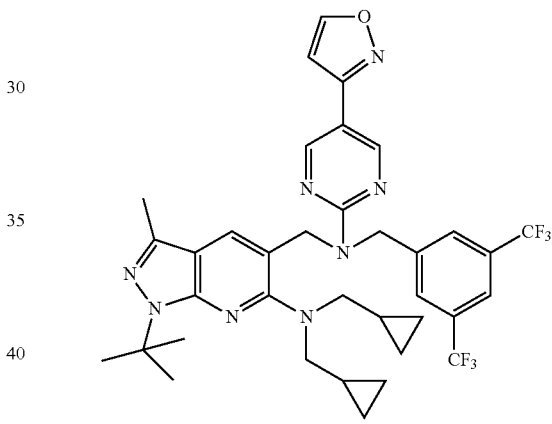

To a mixture of (E)-2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-N-((dimethyl amino)methylene)pyrimidine-5-carboxamide, obtained in Example 6, (0.100 g, 0.130 mmol) in methanol, hydroxylamine hydrochloride (0.03 ml, 0.80 mmol) was added. The resultant mixture was refluxed for 1-2 h. Thereafter the reaction mixture was treated with water and extracted with EtOAc. The combined organic layer was washed with brine, dried over sodium sulfate and concentrated under reduced pressure to obtain a crude product which was further purified by column chromatography using 100-200 mesh silica gel and 5% EtOAc as eluent.

¹H NMR (400 MHz, CDCl₃) δ 8.81 (s, 2H), 8.30 (d, J=1.9 Hz, 1H), 7.74 (s, 3H), 7.62 (s, 3H), 6.45 (d, J=1.9 Hz, 1H), 5.30 (s, 1H), 5.14 (s, 2H), 4.90 (s, 1H), 3.105 (d, J=6.6 Hz, 4H), 2.39 (s, 3H), 1.28 (s, 9H), 0.94-0.86 (m, 2H), 0.37-0.33 (m, 4H), 0.07-0.03 (m, 4H).

MS (m/z): 713 (M⁺+1, 100%).

Example 8

5-(((5-(1H-pyrazol-3-yl)pyrimidin-2-yl)(3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine

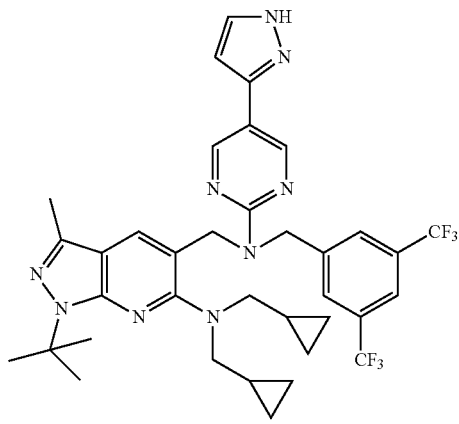 [SMILES: Cc1nn(C(C)(C)C)c2nc(N(CC3CC3)CC3CC3)c(CN(Cc3cc(C(F)(F)F)cc(C(F)(F)F)c3)c3ncc(-c4cc[nH]n4)cn3)cc12]

(E)-N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)-3-(dimethyl amino)acrylamide, obtained in Example 6, (0.100 g, 0.13 mmol) and hydrazine hydrate (0.04 ml, 0.8 mmol) were taken in ethanol. The reaction mixture was stirred for 2 h. The reaction mixture was concentrated under reduced pressure, extracted with EtOAC. The organic layer was washed with brine, dried over $Na_2SO_4$, and concentrated under reduced pressure to get the crude product which was purified with column chromatography using 100-200 silica gel and 30% EtOAc in petroleum ether as eluent.

$^1$H NMR (400 MHz, CDCl3) δ 8.82 (s, 2H), 7.74-7.72 (m, 4H), 7.64 (s, 2H), 6.58 (d, J=2.2 Hz, 1H), 5.11 (s, 2H), 4.88 (s, 2H), 3.10 (d, J=6.6 Hz, 4H), 2.38 (s, 3H), 1.78 (s, 9H), 0.96-0.86 (m, 2H), 0.37-0.33 (m, 4H), 0.016-0.008 (m, 4H). MS (m/z): 712 (M+1, 100%).

Example 9

5-(((3,5-Bis(trifluoromethyl)benzyl)(5-(1-methyl-1H-pyrazol-3-yl)pyrimidin-2-yl)amino)methyl)-1-(tert-butyl)-N,N-bis(cyclopropylmethyl)-3-methyl-1H-pyrazolo[3,4-b]pyridin-6-amine

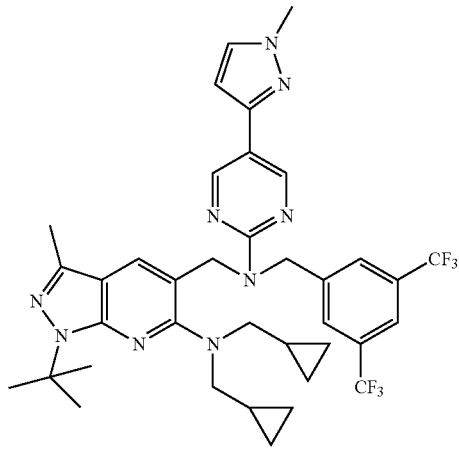 [SMILES: Cc1nn(C(C)(C)C)c2nc(N(CC3CC3)CC3CC3)c(CN(Cc3cc(C(F)(F)F)cc(C(F)(F)F)c3)c3ncc(-c4ccn(C)n4)cn3)cc12]

Sodium hydride (0.008 g, 0.21 mmol) in DMF (2 ml) was added dropwise with stirring to 5-(((5-(1H-pyrazol-3-yl)pyrimidin-2-yl)(3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine, obtained in Example 8 (0.03 g, 0.042 mmol). The reaction mixture was stirred for 20 min at 0° C. CH$_3$I was added at this temperature and the mixture was stirred for an hour at 20-35° C. The reaction mixture was then treated with water and the mixture was extracted three times with ethyl acetate (50 ml). The combined organic layer was washed with brine, dried over $Na_2SO_4$ and concentrated under reduced pressure to get the crude product. The crude product was further purified by column chromatography using 60-120 silica gel and 35% EtOAc in petroleum ether as eluent to afford the title compound.

$^1$H NMR (400 MHz, CDCl$_3$) δ 8.01 (s, 2H), 7.74 (m, 4H), 6.50 (s, 1H), 5.17 (s, 2H), 4.49 (s, 2H), 3.95 (s, 4H), 2.40 (s, 3H), 1.39 (s, 9H), 0.91-0.88 (m, 2H), 0.39-0.35 (m, 4H), 0.015-0.001 (m, 4H). MS (m/z): 726 (M$^+$+1, 60%).

Example 10

2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carbonitrile

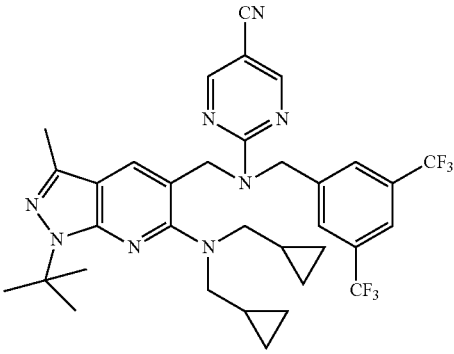 [SMILES: Cc1nn(C(C)(C)C)c2nc(N(CC3CC3)CC3CC3)c(CN(Cc3cc(C(F)(F)F)cc(C(F)(F)F)c3)c3ncc(C#N)cn3)cc12]

5(((3,5-bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine, obtained in step (vi) of Example 1, (0.69 mmol, 0.500 g) was treated with CuCN (0.0.69 mmol, 0.06 g). DMF (5 ml) was added to this reaction mixture and the mixture was heated at 160° C. for 12-16 h. The mixture was then poured into crushed ice causing precipitation of a solid. The precipitate was filtered and purified by column chromatography using 15% EtOAc in petroleum ether as eluent.

$^1$H NMR (400 MHz, CDCl$_3$) δ 8.65 (d, J=10.0 Hz, 2H), 7.75 (s, 1H), 7.70 (s, 2H), 7.50 (s, 1H), 5.10 (s, 2H), 4.80 (s, 2H), 3.10 (d, J=6.4 Hz, 4H), 2.40 (s, 3H), 1.70 (s, 9H), 0.80 (m, 2H), 0.36 (m, 4H), 0.00 (m, 4H). MS (m/z): 671 (M$^+$+1, 100%).

Example 11

2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxamide

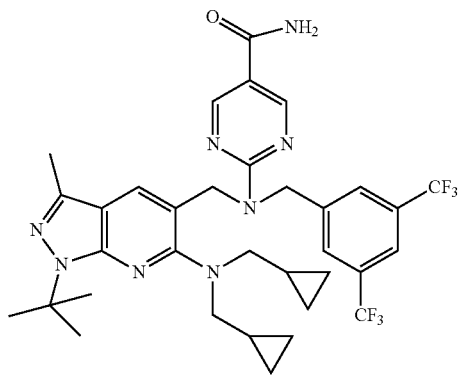 [SMILES: Cc1nn(C(C)(C)C)c2nc(N(CC3CC3)CC3CC3)c(CN(Cc3cc(C(F)(F)F)cc(C(F)(F)F)c3)c3ncc(C(N)=O)cn3)cc12]

2-(((6-(Bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carbonitrile obtained in Example 10, (0.000074 mmol, 0.050 g) in ethanol was treated with 1% solution of KOH (5 ml) and catalytic amount of hydrogen peroxide. The reaction mixture was heated at 40° C. for 30 min. The reaction mixture was then concentrated under reduced pressure, treated with water and extracted with EtOAc. The organic layer was dried over sodium sulfate, concentrated under reduced pressure, and purified by column chromatography using silica gel and 40% EtOAc in petroleum ether as eluent to obtain the title compound.

$^1$H NMR (400 MHz, CDCl$_3$) δ 8.87 (s, 2H), 7.90 (s, 2H), 7.77 (s, 2H), 7.65 (s, 1H), 5.09 (s, 2H), 5.01 (s, 2H), 3.00 (d, J=6.4 Hz, 4H), 2.28 (s, 3H), 1.67 (s, 9H), 0.80 (m, 2H), 0.27 (m, 4H), 0.00 (m, 4H). MS (m/z): 689 (M$^+$+1, 100%).

Example 12

2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-N,N-dimethylpyrimidine-5-carboxamide

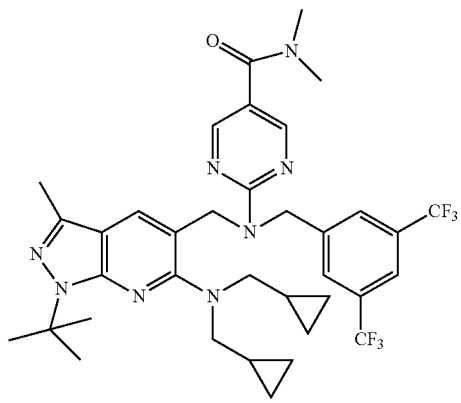 [SMILES: Cc1nn(C(C)(C)C)c2nc(N(CC3CC3)CC3CC3)c(CN(Cc3cc(C(F)(F)F)cc(C(F)(F)F)c3)c3ncc(C(=O)N(C)C)cn3)cc12]

2-(((6-(Bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxamide, obtained in Example 11, (0.0000072 mmol, 0.005 g) in DMF (ml) was treated with sodium hydride (0.000014 mmol, 0.0003 g) and methyl iodide (0.000014 mmol, 0.002 g). The reaction mixture was stirred at 20-35° C. for 1 h. The reaction mixture was then treated with water, extracted with ethyl acetate, dried over sodium sulphate, concentrated under reduced pressure and purified with column chromatography using 20% EtOAc in petroleum ether as eluent to get the title compound.

$^1$H NMR (400 MHz, CDCl$_3$) δ 8.57 (s, 2H), 7.72 (s, 3H), 7.61 (s, 1H), 5.10 (s, 2H), 4.80 (s, 2H), 3.10 (s, 6H), 3.00 (d, J=6.0 Hz, 4H), 2.40 (s, 3H), 1.78 (s, 9H), 0.40 (m, 4H), 0.00 (m, 4H). MS (m/z): 717 (M$^+$+1, 100%).

Example 13

3-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)oxazolidin-2-one

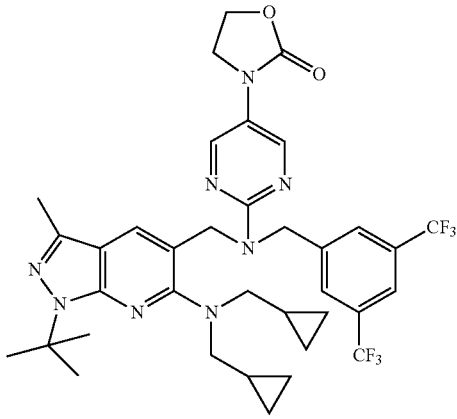 [SMILES: Cc1nn(C(C)(C)C)c2nc(N(CC3CC3)CC3CC3)c(CN(Cc3cc(C(F)(F)F)cc(C(F)(F)F)c3)c3ncc(N4CCOC4=O)cn3)cc12]

5-(((3,5-Bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine, obtained in step (vi) of Example 1 and oxazolidin-2-one (0.15 g, 0.22 mmol) were taken in 1,4-dioxane (5 mL). To this CuI (0.004 g, 0.22 mmol), cyclohexylamine (0.005 g, 0.048 mmol) and K$_2$CO$_3$ (0.06 g, 0.44 mmol) were added. The reaction mixture was degassed with Argon for 15 min. Thereafter it was stirred at a temperature of 114° C. at 40-50 psi for 3 days. The reaction mixture was then filtered through celite, concentrated under reduced pressure, and purified through column chromatography using 60-120 mesh silica gel and 20% EtOAc in petroleum ether as eluent to obtain the title compound as white solid.

$^1$H NMR (400 MHz, CDCl$_3$) δ 8.59 (s, 2H), 7.72-7.70 (m, 3H), 7.61 (s, 1H), 5.07 (s, 2H), 4.83 (s, 2H), 4.55 (t, J=7.6 Hz, 2H), 4.04 (t, J=8.0 Hz, 2H), 3.09 (d, J=6.4 Hz, 4H), 2.40 (s, 3H), 1.78 (s, 9H), 0.92-0.88 (m, 2H), 0.39 (q, J=8.4 Hz, 4H), 0.03-0.00 (m, 4H).

MS (m/z): 731 (M$^+$+1, 100%).

Example 14

5-(((3,5-Bis(trifluoromethyl)benzyl)(5-morpholinopyrimidin-2-yl)amino)methyl)-1-(tert-butyl)-N,N-bis(cyclopropylmethyl)-3-methyl-1H-pyrazolo[3,4-b]pyridin-6-amine

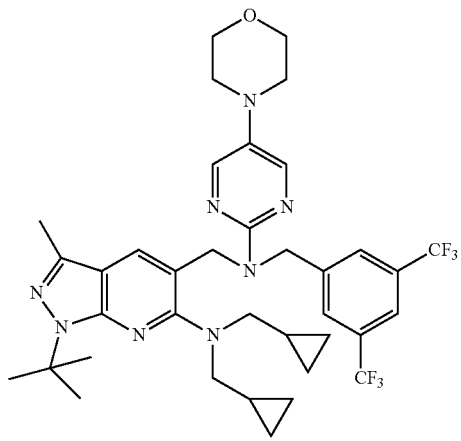 [SMILES: Cc1nn(C(C)(C)C)c2nc(N(CC3CC3)CC3CC3)c(CN(Cc3cc(C(F)(F)F)cc(C(F)(F)F)c3)c3ncc(N4CCOCC4)cn3)cc12]

Toluene was added to a mixture of 5(((3,5-bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine (0.25 g, 0.345 mmol), obtained in step (vi) of Example 1, Pd$_2$(dba)$_3$ (0.053 g, 0.05 mmol), 2-(biphenyl)di-tert-butylphosphine (0.0012 g, 0.04 mmol), NaOtBu (0.05 g, 0.52 mmol) and morpholine (0.045 g, 0.52 mmol). The resultant mixture was heated to reflux for 4 h. Thereafter the reaction mixture was cooled to 20-35° C., treated with water, and extracted with EtOAc. The combined organic layer was washed with brine, dried over sodium sulphate, concentrated under reduced pressure and purified by column chromatography using 15% EtOAc in petroleum ether as eluent to obtain the title compound.

$^1$H NMR (400 MHz, CDCl$_3$) δ 8.17 (s, 2H), 7.70 (s, 3H), 7.61 (s, 1H), 5.02 (s, 2H), 4.81 (s, 2H), 3.89-3.87 (m, 4H), 3.08-3.06 (m, 8H), 2.38 (s, 2H), 0.89-0.86 (m, 2H), 0.34-0.31 (m, 4H), 0.08-0.009 (m, 4H). MS (m/z): 731 (M$^+$+1, 100%).

Example 15

5-(((3,5-bis(trifluoromethyl)benzyl)(5-morpholinopyrimidin-2-yl)amino)methyl)-N,N-bis(cyclopropylmethyl)-1,3-dimethyl-1H-pyrazolo[3,4-b]pyridin-6-amine

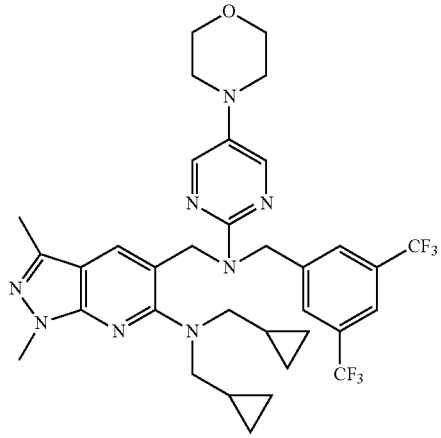 [SMILES: Cc1nn(C)c2nc(N(CC3CC3)CC3CC3)c(CN(Cc3cc(C(F)(F)F)cc(C(F)(F)F)c3)c3ncc(N4CCOCC4)cn3)cc12]

Step (i): Preparation of 5-(((3,5-bis(trifluoromethyl)benzyl)(5-bromopyrimidin-2-yl)amino)methyl)-N,N-bis(cyclopropylmethyl)-1,3-dimethyl-1H-pyrazolo[3,4-b]pyridin-6-amine

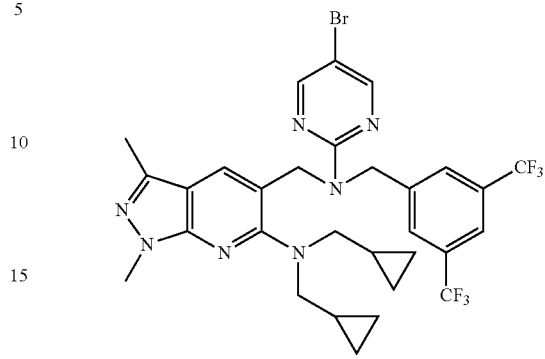

The title compound was synthesized using a procedure substantially similar to that of step (vi) of Example 1 and by using appropriate starting materials.

$^1$H NMR (400 MHz, CDCl$_3$) δ 8.4 (s, 2H), 7.58 (s, 1H), 7.65 (s, 2H), 7.71 (s, 1H), 5.03 (s, 2H), 4.77 (s, 2H), 3.96 (s, 3H), 3.13 (s, 2H), 3.11 (s, 2H), 2.39 (s, 3H), 0.94-0.86 (m, 2H), 0.39-0.35 (m, 4H), 0.08-0.04 (m, 4H). MS (m/z): 684 (M$^+$+2, 100%).

Step (ii): Preparation of 5-(((3,5-bis(trifluoromethyl)benzyl)(5-morpholinopyrimidin-2-yl)amino)methyl)-N,N-bis(cyclopropylmethyl)-1,3-dimethyl-1H-pyrazolo[3,4-b]pyridin-6-amine The title compound was obtained by a procedure substantially similar to that of Example 14, by using 5-(((3,5-bis (trifluoromethyl)benzyl)(5-bromopyrimidin-2-yl)amino) methyl)-N,N-bis(cyclopropylmethyl)-1,3-dimethyl-1H-pyrazolo[3,4-b]pyridin-6-amine obtained from above step as the reactant.

$^1$H NMR (400 MHz, CDCl$_3$) δ 8.19 (s, 2H), 7.68 (s, 1H), 7.61 (s, 1H), 7.60 (s, 2H), 5.03 (s, 2H), 4.79 (s, 2H), 3.97 (s, 3H), 3.91-3.87 (m, 4H), 3.09 (m, 4H), 2.38 (s, 3H), 0.93-0.88 (m, 2H), 0.37-0.35 (m, 4H), 0.14-0.01 (m, 4H). MS (m/z): 689 (M$^+$+1, 100%).

Example 16

1-(2-(((6-(Bis(cyclopropylmethyl)amino)-1-(tert-butyl)-3-methyl-1H-pyrazolo[3,4-b]pyridin-5-yl) methyl)(3,5-bis(trifluoromethyl)benzyl)amino)pyrimidin-5-yl)pyrrolidin-2-one

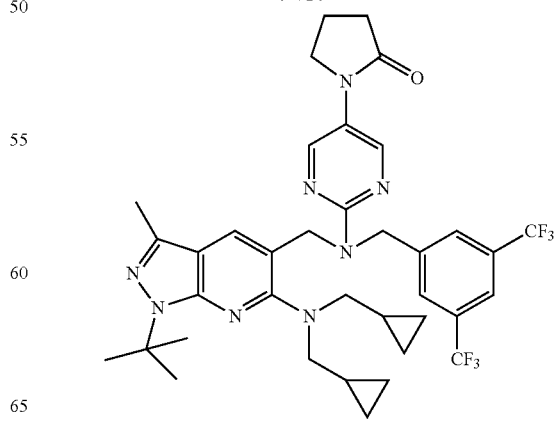

5-(((3,5-Bis(trifluoromethyl)benzyl)(5-bromopyrimidin-2-yl)amino)methyl)-1-(tert-butyl)-N,N-bis(cyclopropylmethyl)-3-methyl-1H-pyrazolo[3,4-b]pyridin-6-amine (0.2 g, 0.293 mmol), obtained in step (vi) of Example 1,2-pyrrolidinone (0.024 g, 0.293 mmol), CuI (0.005 mg, 0.029 mmol), trans-1,2-diaminocyclohexane (0.007 g, 0.064 mmol) were taken in a sealed tube in 1,4-dioxane (5 mL), which was degassed with argon for 15 min. K₂CO₃ (0.08 g, 0.586 mmol) was added to it. The reaction mixture was stirred at 100° C. for 28 h. Thereafter the reaction mixture was filtered through celite, extracted with EtOAc. The combined organic layer was washed with water, dried over Na₂SO₄, concentrated under reduced pressure, and purified by column chromatography using EtOAc-petroleum ether as eluent to obtain the title compound.

¹H NMR (400 MHz, CDCl₃) δ 8.66 (s, 2H), 7.71 (s, 3H), 7.61 (s, 1H), 5.06 (s, 2H), 4.83 (s, 2H), 3.84 (t, J=6.8 Hz, 2H), 3.09 (d, J=6.4 Hz, 4H), 2.61 (t, J=8.0 Hz, 2H), 2.40 (s, 3H), 2.27-2.22 (m, 2H), 1.78 (s, 9H), 0.91-0.36 (m, 2H), 0.34 (q, J=8.4 Hz, 4H), 0.03-0.00 (m, 4H).

MS (m/z): 729 (M⁺+1, 100%).

Example 17

Ethyl-2(((6-(bis(cyclopropylmethyl)amino)-1-(tert-butyl)-3-methyl-1H-pyrazolo[3,4-b]pyridin-5-yl) methyl)(3,5-bis(trifluoromethyl)benzyl)amino)-4-methylpyrimidine-5-carboxylate

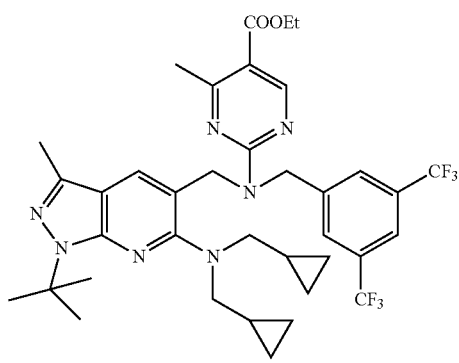 [SMILES: Cc1nc(N(Cc2cc(C(F)(F)F)cc(C(F)(F)F)c2)Cc2cc3c(C)nn(C(C)(C)C)c3nc2N(CC2CC2)CC2CC2)ncc1C(=O)O]

To 5-(((3,5-bis(trifluoromethyl)benzyl)amino)methyl)-1-(tert-butyl)-N,N-bis(cyclopropyl methyl)-3-methyl-1H-pyrazolo[3,4-b]pyridin-6-amine, obtained in step (v) of Example 1, (0.8 g, 1.4 mmol) was dissolved in DMF (8 ml), ethyl-2-chloro-4-methyl pyrimidine-5-carboxylate (0.29 g, 1.4 mmol), fused potassium carbonate (0.58 g, 2.8 mmol) were added to the above solution and the resultant mixture was heated at 70° C. for 2 h. The reaction mixture was then poured into water and extracted with EtOAc. The organic layer was washed with water, dried over sodium sulphate, concentrated under reduced pressure and purified by column chromatography using 60-120 silica gel and 5% EtOAc in petroleum ether as eluent to obtain the title compound (yield: 30%).

¹H NMR (400 MHz, CDCl₃) δ 8.90 (bs, 1H), 7.80-7.60 (m, 4H), 5.10 (s, 2H), 4.90 (s, 2H), 3.10 (m, 4H), 2.70 (s, 3H), 2.40 (s, 3H), 0.80 (m, 2H), 0.40 (m, 4H), 0.10 (m, 4H).

MS (m/z): 732 (M⁺+1, 100%).

Example 18

2-(((6-(Bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-4-methylpyrimidine-5-carboxylic acid

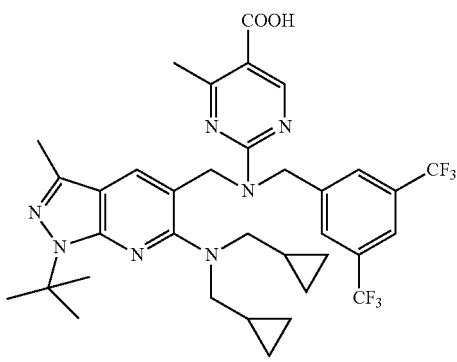

Ethyl 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)-4-methylpyrimidine-5-carboxylate, obtained in Example 17, (0.120 g, 0.16 mmol) was dissolved in EtOH (6 ml) and 10% NaOH (4 ml) was added to it. The reaction mixture was stirred at 20-35° C. for 3 h. The reaction mixture was then acidified with citric acid solution, extracted with EtOAc, washed with water, dried over sodium sulphate, and concentrated under reduced pressure to obtain the crude product. This product was further purified by column chromatography using 60-120 silica gel and 20% EtOAc in petroleum ether as eluent to get the desired product (yield: 14%).

¹H NMR (400 MHz, CDCl₃) δ 8.90 (bs, 1H), 7.80-7.60 (m, 4H), 5.1 (s, 2H), 4.90 (s, 2H), 3.10 (m, 2H), 2.70 (s, 3H), 2.40 (s, 3H), 0.80 (m, 2H), 0.40 (m, 4H), 0.10 (m, 4H).

MS (m/z): 704 (M⁺+1, 100%).

Example 19

Ethyl 2-(((6-(bis(cyclopropylmethyl)amino)-1-(tert-butyl)-3-methyl-1H-pyrazolo[3,4-b]pyridin-5-yl) methyl)(3,5-bis(trifluoromethyl)benzyl)amino)pyrimidine-5-carboxylate

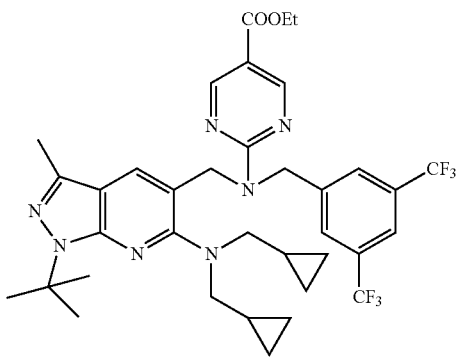

5-(((3,5-bis(trifluoromethyl)benzyl)amino)methyl)-1-(tert-butyl)-N,N-bis(cyclopropyl methyl)-3-methyl-1H-pyrazolo[3,4-b]pyridin-6-amine, obtained in step (v) of Example 1, (0.8 g, 1.4 mmol) was dissolved in DMF (8 ml).

Ethyl 2-chloropyrimidine-5-carboxylate (0.58 g, 1.4 mmol), fused potassium carbonate (0.58 g, 2.8 mmol) were added to the above solution and the resultant mixture was heated at 70° C. for 2 h. The reaction mixture was then poured into water and extracted with EtOAc. The organic layer was washed with water, dried over sodium sulphate, concentrated under reduced pressure and purified by column chromatography using 60-120 silica gel and 5% EtOAc in petroleum ether as eluent to obtain the title compound (yield 30%).

$^1$H NMR (400 MHz, CDCl$_3$) δ 8.90 (bs, 1H), 7.80-7.60 (m, 4H), 5.10 (s, 2H), 4.90 (s, 2H), 4.30 (m, 2H), 3.10 (m, 4H), 2.70 (s, 3H), 2.40 (s, 3H), 1.40 (t, 3H), 0.80 (m, 2H), 0.40 (m, 4H), 0.10 (m, 4H). MS (m/z): 732 (M$^+$+1, 100%).

Example 20

2-(((6-(Bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxylic acid

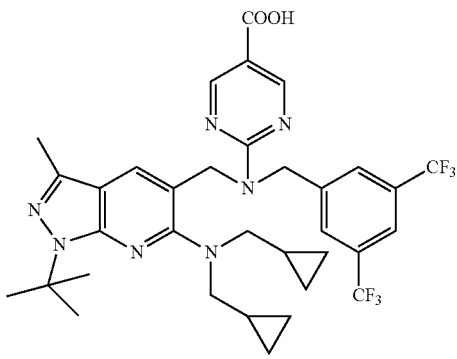 [SMILES: Cc1nn(C(C)(C)C)c2nc(N(CC3CC3)CC3CC3)c(CN(Cc3cc(C(F)(F)F)cc(C(F)(F)F)c3)c3ncc(C(=O)O)cn3)cc12]

The title compound was prepared by a procedure substantially similar to that used for Example 18 using ethyl 2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidine-5-carboxylate, obtained in Example 19 as a starting material.

$^1$H NMR (400 MHz, CDCl$_3$) δ 13 (bs, 1H), 8.77 (s, 2H), 7.90 (s, 1H), 7.77 (s, 2H), 7.68 (s, 1H), 5.11 (s, 2H), 5.02 (s, 2H), 3.05 (d, J=6, 4H), 2.28 (s, 3H), 1.67 (s, 9H), 0.8 (m, 2H), 0.27 (dd, J=12.6, J=5.18, 4H), 0.04 (dd, J=9.46, J=4.8, 4H). MS (m/z): 690 (M$^+$+1, 100%), 325 (50%).

Example 21

Determination of in Vitro CETP Activity Using Fluorometric Technique

An in vitro cholesteryl ester transfer protein inhibition (CETP) assay using a commercially available fluorometric assay kit from ROAR Biomedicals, USA was used to measure the CETP inhibition activity of the compounds of this application. This assay kit uses a donor molecule containing a fluorescent self-quenched neutral lipid that is transferred to an acceptor molecule in the presence of recombinant CETP enzyme (rCETP). The CETP-mediated transfer of the fluorescent neutral lipid to the acceptor molecule results in an increase in fluorescence (Excitation: 492 nm; Emission: 516 nm).

20 mM stock solutions of compounds were prepared in 100% DMSO and further dilutions were made such that the final concentration of DMSO in the reaction mix was 1%. The reactions were performed as suggested by the kit manufacturer as follows. The assay was performed in 96 well microplates and in each well, the reaction mixture contained 190 μl of assay buffer (150 mM NaCl, 10 mM Tris and 2 mM EDTA, pH-7.4), 4 μl of donor particle, 4 μl of acceptor particle, rCETP (50 ng) and 2 μl of test compound at varying final concentration of 0.1, 1, 10, 100, 1000 & 10000 nM. Two control reactions were performed, one without test compound (positive control) and the other without the rCETP (negative control). The reactions were incubated at 37° C. for 90 minutes and the reaction plate was transferred to a PCR machine MX3005P and the fluorescence units (FLU) were quantified (Excitation: 492 nm; Emission: 516 nm).

The negative control values were subtracted from the positive control as well as all the test values to correct for background fluorescence. The percentage inhibition of activity was calculated by using the following equation:

% Inhibition of CETP activity=[100−(100×(FLU in test/FLU in positive control))].

The half maximal inhibitory concentration (IC$_{50}$) was determined using the BIOGRAPH software (version no. 3.3).

Using this protocol, various compounds as described herein were found to exhibit inhibitory effect on CETP, as shown in the below table:

| Example No. | IC50 (nM) |
|---|---|
| 1 | 64 |
| 2 | 78 |
| 3 | 35 |
| 4 | 5.7 |
| 5 | 41.5 |
| 7 | 9.4 |
| 8 | 27 |
| 9 | 100 |
| 10 | 1250 |
| 11 | 18 |
| 12 | 215 |
| 13 | 10 |
| 14 | 46 |
| 15 | 49 |
| 16 | 56 |
| 18 | 54 |
| 19 | 70 |
| 20 | 61 |

Example 22

Determination of Qualitative and Quantitative Changes of HDL-C in the Hamster Model of Dyslipidemia.

Male Golden Syrian hamsters (*Mesocricetus auratus*) were procured from local sources. After acclimatization period of one week on high fat diet (10% coconut oil, 0.2% cholesterol), animals were bled and randomized into vehicle or drug treatment groups based on plasma HDL-C prior to initiating drug therapy. The animals were bled after 7 days of dosing, plasma total cholesterol, HDL-C, triglycerides were measured spectrophotometrically using commercially available kits. The percent elevation was calculated according to the formula: [(TT/OT)/(TC/OC)]−1×100, percent reduction was calculated according to the formula: 1-[(TT/OT)/(TC/OC)]×100, where TT is the test day treated, OT the zero day treated, TC the test day control and OC the zero day control. Statistical significance for differences between the groups was by one way analysis of variance (ANOVA), followed by Dunnett's test. P<0.05 was considered significant. Significant difference for treatment group Vs vehicle group was determined by student's t-test. P<0.05 was considered significant. Pooled plasma samples from each treatment group after 7 days of dosing were also fractionated by FPLC using Superose 6 and Superdex 200 columns connected in tandem, into the major lipoprotein classes, VLDL, LDL, and HDL. Fractions for all samples were assayed for total cholesterol using the Amplex Red Cholesterol Assay kit (Molecular Probes, USA). It was found that the compounds as described herein showed remarkable effects in terms of their dose-dependent and significant effect on in vivo HDL-C elevation accompanied by appearance of large size HDL-2 subclass, characteristic of in vivo CETP inhibition.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof.

What is claimed is:
1. A compound having the formula (Ic):

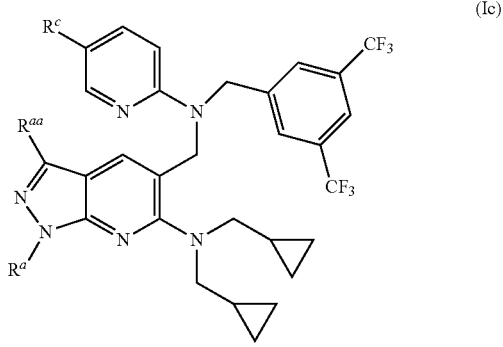

(Ic)

or a stereoisomer thereof or a pharmaceutically acceptable salt thereof, wherein
$R^a$ and $R^{aa}$ are independently of each other selected from hydrogen or alkyl; and
$R^c$ is selected from hydrogen, cyano, halogen, alkyl, alkoxy, haloalkoxy, —COOR$^d$, —C(=O)—R$^e$, —CONR$^g$R$^h$, —C(=O)—CH=CH—NR$^i$R$^j$, —NH-COR$^t$, an optionally substituted group selected from cycloalkyl, aryl, heteroaryl or heterocycle ring, wherein the optional substituent, in each occurrence, is selected independently from hydrogen, halogen, cyano, hydroxyl, alkyl, haloalkyl, alkoxy, alkoxyalkyl or haloalkoxy.

2. A compound, which is selected from the group consisting of:
N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl) isobutyramide,
5-(((3,5-bis(trifluoromethyl)benzyl)(5-cyclopropylpyridin-2-yl)amino)methyl)-1-(tert-butyl) -N,N-bis(cyclopropylmethyl)-3-methyl-1H-pyrazolo[3,4-b]pyridin-6-amine,
N-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5 -yl)cyclopropane carboxamide,
1-(2-(((6-(bis(cyclopropylmethyl)amino)-1,3-dimethyl-1H-pyrazolo[3,4-b]pyridin-5-yl)methyl)(3,5-bis(trifluoromethyl)benzyl)amino)pyrimidin-5-yl)ethanone,
1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)ethanone,
(E)-1-(2-(((6-(bis(cyclopropylmethyl)amino)-1-(tert-butyl)-3-methyl-1H-pyrazolo[3,4-b]pyridin-5-yl)methyl) (3,5 -bis(trifluoromethyl)benzyl)amino)pyrimidin-5-yl)-3-(dimethylamino)prop-2-en-1-one,
5(((3,5-bis(trifluoromethyl)benzyl)(5-(isoxazol-3-yl)pyrimidin-2-yl)amino)methyl)-N,N-bis(cyclopropylmethyl)-1,3-dimethyl-1H-pyrazolo[3,4-b]pyridin-6-amine,
5-(((5-(1H-pyrazol-3-yl)pyrimidin-2-yl)(3,5-bis(trifluoromethyl)benzyl)amino)methyl)- 1-(tert-butyl)-N,N-bis (cyclopropylmethyl)-3-methyl-1H-pyrazolo [3,4-b] pyridin-6-amine,
5-(((3,5-bis(trifluoromethyl)benzyl)(5-(1-methyl-1H-pyrazol-3-yl)pyrimidin-2-yl)amino)methyl)-1-(tert-butyl)-N,N-bis(cyclopropylmethyl)-3-methyl-1 H-pyrazolo [3,4-b]pyridin-6-amine,
2-(((6-(bis(cyclopropylmethyl)amino)- 1-(tert-butyl)-3-methyl- 1H-pyrazolo [3,4-b]pyridin-5-yl)methyl)(3,5-bis(trifluoromethyl)benzyl)amino)pyrimidine-5-carbonitrile,
2-(((6-(bis(cyclopropylmethyl)amino)-1-(tert-butyl)-3-methyl-1H-pyrazolo [3,4-b]pyridin-5-yl)methyl)(3,5-bis(trifluoromethyl)benzyl)amino)pyrimidine-5-carboxamide,
2-(((6-(bis(cyclopropylmethyl)amino)- 1-(tert-butyl)-3-methyl- 1H-pyrazolo [3 ,4-b]pyridin-5-yl)methyl)(3,5-bis(trifluoromethyl)benzyl)amino)-N,N-dimethylpyrimidine -5-carboxamide,
3-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)oxazolidin-2-one,
5-3,5-bis(trifluoromethyl)benzyl)(5-morpholinopyrimidin-2-yl)amino)methyl)-1-(tert-butyl)-N,N-bis(cyclopropylmethyl)-3-methyl-1H-pyrazolo [3,4-b ]pyridin-6-amine,
5-(((3,5-bis(trifluoromethyl)benzyl)(5-morpholinopyrimidin-2-yl)amino)methyl)-N,N-bis(cyclopropylmethyl)-1,3-dimethyl-1H-pyrazolo[3,4-b]pyridin-6-amine,
1-(2-(((6-(bis(cyclopropylmethyl)amino)-1-(tert-butyl)-3-methyl-1H-pyrazolo[3,4-b]pyridin-5-yl)methyl)(3,5-bis(trifluoromethyl)benzyl)amino)pyrimidin-5-yl)pyrrolidin-2-one,
Ethyl-2-(((6-(bis(cyclopropylmethyl)amino)-1-(tert-butyl)-3-methyl-1H-pyrazolo[3,4-b]pyridin-5-yl)methyl) (3,5-bis(trifluoromethyl)benzyl)amino)-4-methylpyrimidine-5-carboxylate,
2-(((6-(bis(cyclopropylmethyl)amino)-1-(tert-butyl)-3-methyl-1H-pyrazolo [3 ,4-b]pyridin-5-yl)methyl)(3,5-bis(trifluoromethyl)benzyl)amino)-4-methylpyrimidine -5-carboxylic acid,
Ethyl-2-(((6-(bis(cyclopropylmethyl)amino)-1-(tert-butyl)-3-methyl-1H-pyrazolo[3,4-b]pyridin-5-yl)methyl) (3,5-bis(trifluoromethyl)benzyl)amino)pyrimidine-5-carboxylate,
2-(((6-(bis(cyclopropylmethyl)amino)-1-(tert-butyl)-3-methyl-1H-pyrazolo [3 ,4-b]pyridin-5-yl)methyl)(3,5-bis(trifluoromethyl)benzyl)amino)pyrimidine-5-carboxylic acid,
5-(((3,5-bis(trifluoromethyl)benzyl)amino)methyl)-1-(tert-butyl)-N,N-bis(cyclopropylmethyl)-3-methyl-1H-pyrazolo[3,4-b]pyridin-6-amine, and 5-(((3,5-bis(trifluoromethyl)benzyl)(5-bromopyrimidin-2-yl)amino) methyl)-1-(tert-butyl) -N,N-bis(cyclopropylmethyl)-3-methyl- 1H-pyrazolo [3,4-b ]pyridin-6-amine;

or a stereoisomer thereof or a pharmaceutically acceptable salt thereof.

3. A pharmaceutical composition comprising at least one compound according to claim 2 and at least one pharmaceutically acceptable excipient.

4. A method of inhibiting cholesteryl ester-transfer protein (CETP) in a patient comprising administering to said patient a therapeutically effective amount of a compound according to claim 2.

5. A method of increasing high density lipoprotein (HDL) cholesterol in a patient comprising administering to said patient a therapeutically effective amount of a compound according to claim 2.

6. A method of lowering low density lipoprotein (LDL) cholesterol in a patient comprising administering to said patient a therapeutically effective amount of a compound according to claim 2.

7. A method of binding cholesteryl ester-transfer protein in a patient comprising administering to said patient a therapeutically effective amount of a compound according to claim 2.

8. A pharmaceutical composition comprising at least one compound of claim 3 or a stereoisomer thereof or a pharmaceutically acceptable salt thereof and at least one pharmaceutically acceptable excipient.

9. A method of inhibiting cholesteryl ester-transfer protein (CETP in a patient comprising administering to said patient a therapeutically effective amount of a compound according to claim 2.

10. A method of increasing high density lipoprotein (HDL) cholesterol in a patient comprising administering to said patient a therapeutically effective amount of a compound according to claim 2.

11. A method of lowering low density lipoprotein (LDL) cholesterol in a patient comprising administering to said patient a therapeutically effective amount of a compound according to claim 2.

12. A method of binding cholesteryl ester-transfer protein in a patient comprising administering to said patient a therapeutically effective amount of a compound according to claim 2.

* * * * *